US008524678B2

(12) United States Patent
Watkins et al.

(10) Patent No.: US 8,524,678 B2
(45) Date of Patent: Sep. 3, 2013

(54) METHOD FOR DELIVERING GENES

(75) Inventors: Linda May Rothblum Watkins, Boulder, CO (US); Travis Hughes, Boulder, CO (US); Raymond A. Chavez, Alameda, CA (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 7 days.

(21) Appl. No.: 11/920,712

(22) PCT Filed: May 26, 2006

(86) PCT No.: PCT/US2006/020864

§ 371 (c)(1), (2), (4) Date: Sep. 2, 2008

(87) PCT Pub. No.: WO2006/130581

PCT Pub. Date: Dec. 7, 2006

(65) Prior Publication Data

US 2009/0208563 A1 Aug. 20, 2009

Related U.S. Application Data

(60) Provisional application No. 60/686,324, filed on May 31, 2005.

(51) Int. Cl.

*A01N 43/04* (2006.01)
*C12N 15/00* (2006.01)
*C12N 15/63* (2006.01)
*C07H 21/04* (2006.01)

(52) U.S. Cl.

USPC ......... 514/44; 435/320.1; 435/455; 536/23.5; 536/24.1

(58) Field of Classification Search

USPC ............... 514/44; 435/320.1, 455; 536/23.5, 536/24.1

See application file for complete search history.

(56) References Cited

U.S. PATENT DOCUMENTS

| | | | | |
|---|---|---|---|---|
| 5,231,012 | A | 7/1993 | Mosmann et al. | |
| 6,018,036 | A | 1/2000 | Mosmann et al. | |
| 6,165,754 | A | 12/2000 | Crystal et al. | |
| 6,217,857 | B1 | 4/2001 | Mosmann et al. | |
| 6,413,942 | B1 | 7/2002 | Felgner et al. | |
| 6,428,985 | B1 | 8/2002 | Bromberg et al. | |
| 6,652,850 | B1 * | 11/2003 | Philip et al. | 424/93.21 |
| 7,749,490 | B2 | 7/2010 | Sommer et al. | |
| 2003/0044384 | A1 | 3/2003 | Roberts et al. | |
| 2003/0049256 | A1 | 3/2003 | Tobinick | |
| 2003/0130221 | A1 | 7/2003 | High et al. | |
| 2003/0232781 | A1 * | 12/2003 | Wolffe et al. | |
| 2004/0142893 | A1 * | 7/2004 | Ikeda et al. | |
| 2004/0258671 | A1 * | 12/2004 | Watkins | |
| 2010/0028296 | A1 | 2/2010 | Chavez et al. | |

FOREIGN PATENT DOCUMENTS

| | | |
|---|---|---|
| WO | WO 99/47157 | 9/1999 |
| WO | WO 99/56784 | 11/1999 |
| WO | WO 2005/000215 | 1/2005 |

OTHER PUBLICATIONS

Goudy et al., 2001, PNAS, vol. 98, No. 24, pp. 13913-13918.*
Verma et al., 1997, Nature, vol. 389, pp. 239-242.*
Eck et al., 1996, Goodman & Gilman's The Pharmacological Basis of Therapeutics, McGraw-Hill, New York, p. 77-101.*
Gorecki, D., 2001, Expert Opin. Emerging Drugs, 6(2): 187-198.*
Kodama et al., 2006, Current Medicinal Chemistry, vol. 13, p. 2155-2161.*
Nishikawa et al., 2001, Human Gene Therapy, vol. 12, p. 861-870.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
Milligan et al., "Repeated Intrathecal Injections of Plasmid DNA Encoding Interleukin-10 Produce Prolonged Reversal of Neuropathic Pain", Pain 126:294-308 (2006).
Milligan et al., "Controlling Pathological Pain by Adenovirally Driven Spinal Production of the Anti-Inflammatory Cytokine, Interleukin-10", European Journal of Neuroscience, 21:2136-2148 (2005).
Milligan et al., "Controlling Neuropathic Pain by Adeno-Associated Virus Driven Production of the Anti-Inflammatory Cytokine, Interleukin-10", Molecular Paid, I:9 (2005), doi:10.1186/1744-8069-I-9.
Mu et al., "IL-10 Suppresses Chemokines, Inflammation, and Fibrosis in a Model of Chronic Renal Disease," J. Am. Soc. Nephrol., 16:3651-3660 (2005).
Office Action dated Aug. 21, 2009 issued in U.S. Appl. No. 11/920,711.
Office Action dated Jul. 21, 2006 issued in U.S. Appl. No. 10/742,641.
Office Action dated Dec. 2, 2005 issued in U.S. Appl. No. 10/742,641.
Office Action dated May 25, 2010 issued in U.S. Appl. No. 12/291,752.
Office Action dated Nov. 16, 2009 issued in U.S. Appl. No. 12/291,752.
Office Action dated May 27, 2008 issued in U.S. Appl. No. 11/215,721.
Office Action dated Aug. 27, 2007 issued in U.S. Appl. No. 11/215,721.
Office Action dated Nov. 21, 2005 issued in U.S. Appl. No. 11/215,721.

(Continued)

*Primary Examiner* — Shin-Lin Chen
(74) *Attorney, Agent, or Firm* — Roberta L. Robins; Robins Law Group

(57) ABSTRACT

Methods of delivering transgenes to target cells using plasmids comprising viral inverted terminal repeat (ITR) sequences are described. Such plasmids are capable of directing sustained transgene expression in target cells in rats provided that at least one adeno-associated virus (AAV) ITR sequence is present in the plasmid, regardless of whether that ITR is located upstream or downstream of the transgene. In a particular embodiment, plasmids comprising one or more AAV ITR sequence and an IL-10 transgene are shown to be effective in sustained reversal of pain in an animal model of neuropathic pain.

9 Claims, 12 Drawing Sheets

(56) References Cited

OTHER PUBLICATIONS

Goodman, et al., "Synthesis and Characterization of Rat Interleukin-10 (IL-10) CDNA Clones From the RNA of Cultured OX8-negative OX22-negative Thoracic Duct T Cells", Biochemical and Biophysical Research Communications, 189(1):1-7 (1992).
Vieira, et al. "Isolation and Expression of Human Cytokine Synthesis Inhibitory Factor CDNA Clones: Homology to Epstein-Barr Virus Open Reading Frame BCRF1", Proceedings of the National Academy of Sciences of USA, National Academy of Science, Washington, DC, US, 88:1172-1176 (1991).
Milligan, et al., Society for Neuroscience, 2002, Presentation No. 656.19, Neuroscience 2002 Abstract.
Yang et al., "Sustained Expression of Naked Plasmid DNA Encoding Hepatocyte Growth Factor in Mice Promotes Liver and Overall Body Growth," Hepatology, 2001, vol. 33, pp. 848-859.
Choate et al., "Direct Cutaneous Gene Delivery in a Human Genetic Skin Disease," Human Gene Therapy, 1997, vol. 8, pp. 1659-1665.
Zheng et al., "Administration of Noncytolytic IL-10/Fc in Murine Models of Lipopolysaccharide-Induced Septic Shock and Allogeneic Islet Transplantation," J. of Immunol., 1995, vol. 154, No. 10, pp. 5590-5600.
Wagner et al., "Anti-inflammatory interleukin-10 therapy in CCI neuropathy decreases thermal hyperalgesia, macrophage recruitment, and endoneurial TNF-α expression," Pain, 1998, vol. 74, pp. 35-42.
Raghavendra et al., "The Role of Spinal Neuroimmune Activation in Morphine Tolerance/Hyperalgesia in Neuropathic and Sham-Operated Rats," J. of Neuroscience, 2002, vol. 22, No. 22, pp. 9980-9989.
Japanese Office Action mailed Apr. 21, 2010, in Japanese application No. 2006-517161.
Watkins & Maier, "Immune Regulation of Central Nervous System Functions: From Sickness Responses to Pathological Pain," *J Intern Med* 257:139-155 (2005).
Watkins & Maier, "Glia: A Novel Drug Discovery Target for Clinical Pain," *Nat Rev* 2:973-985 (2003).
Adachi, O. et al., "Gene transfer of Fc-fusion cytokine by in vivo electroporation: application to gene therapy for viral myocarditis," Gene Therapy 9:577-583 (2002).
Hao, S. et al., "Herpes simplex virus (HSV) vector expressing soluble TNF α—receptor and IL—4 produces persistent antinociception in neuropathic pain" Washington D.C., *Society for Neuroscience*, Program No. 131.8 (2003).
Laughlin et al., "Cytokine involvement in dynorphin-induced allodynia" *Pain* 84:159-167 (2000).
Meuli-Simmen et al., Gene expression along the cerebral-spinal axis after regional gene delivery *Human Gene Therapy* 10:2689-2700 (1999).
Okamoto et al., "Pro- and anti-inflammatory cytokine gene expression in rat sciatic nerve chronic constriction injury model of neuropathic pain" *Experimental Neurology* 169:386-391 (2001).
Plunkett et al., "Effects of interleukin-10 (IL-10) on pain behavior and gene expression following excitotoxic spinal cord injury in the rat" *Experimental Neurology* 168:144-154 (2001).
Yao et al., "Interleukin-2 gene has superior antinociceptive effects when delivered intrathecally" *Clinical Neuroscience and Neuropathology* 13(6):791-794 (2002).
Jiang et al., "Sustained Expression of Fc-Fusion Cytokine Following In Vivo Electroporation and Mouse Strain Differences in Expression Levels," *J. Biochem*, 133:423-427 (2003).
Cua et al., "Central Nervous System Expression of IL-10 Inhibits Autoimmune Encephalomyelitis," J. Immunology, Jan. 2001, vol. 166, pp. 603-608.
Andreansky et al., "Treatment of Intracranial Gliomas in Immunocompetent Mice using Herpes Simplex Viruses that Express Murine Interleukins," Gene Therapy, Jan. 1998, vol. 5, pp. 121-130.
Milligan, et al., ($10^{th}$ Congress on Pain: Abstract 392-P26, 135, Aug. 19, 2002.
Pfiefer and Verma (2001) Annu. Rev. Genomics. Hum. Genet. 2:177-211.
Johnson-Saliba et al. (2001) Curr. Drug. Targets 2:371-99.
Shoji et al. (2004) Current Pharmaceutical Design 10:785-796.
Chan (2002) Ocular Immun. Inflam. 10:161-186.
Genbank Accession No. P22301 (Aug. 1, 1991).
Cavazzana-Calvo (The Journal of Clinical Investigation, 117(6):1456-1465 (2007)) in U.S. Appl. No. 12/291,752.
Mata et al (Curr Gene Ther. 8(l):42-48 (2008)) in U.S. Appl. No. 12/291,752.
Sterry et al (Pharmacological Reviews, 55(2):241-269, (2003)) in U.S. Appl. No. 12/291,752.
Storek et al (Molecular Pain, 2(4):1-11 (2006)) in U.S. Appl. No. 12/291,752.
Baron et al., (Nature Clinical Practice, Neurology, 12(2):95-106 (2006)).

* cited by examiner

```
hIL-10  SPGQGTQSENSCTHFPGNLPNMLRDLRDAFSRVK
mIL-10  SRGQYSREDNNCTHFPVGQSHMLLELRTAFSQVK
vIL-10  -----------QCDNFP----QMLRDLRDAFSRVK
        1        10        20        30

TFFQMKDQLDNLLLKESLLEDFKGYLGCQALSEMI
TFFQTKDQLDNILLTDSLMQDFKGYLGCQALSEMI
TFFQTKDEVDNLLLKESLLEDFKGYLGCQALSEMI
     40        50        60

QFYLEEVMPQAENQDPDIKAHVNSLGENLKTLRLR
QFYLVEVMPQAEKHGPEIKEHLNSLGEKLKTLRMR
QFYLEEVMPQAENQDPEAKDHVNSLGENLKTLRLR
70        80        90        100

LRRCHRFLPCENKSKAVEQVKNAFNKLQEKGIYKA
LRRCHRFLPCENKSKAVEQVKSDFNKLQDQGVYKA
LRRCHRFLPCENKSKAVEQIKNAFNKLQEKGIYKA
     110       120       130

MSEFDIFINYIEAYMTMKIRN
MNEFDIFINCIEAYMMIKMKS
MSEFDIFINYIEAYMTIKAR
140       150       160
```

Figure 10

SEQUENCE LISTING

```
<160> NUMBER OF SEQ ID NOS: 5

<210> SEQ ID NO 1
<211> LENGTH: 160
<212> TYPE: PRT
<213> ORGANISM: Homo sapiens

<400> SEQUENCE: 1

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140
```

```
Ile Phe Ile Asn Tyr Ile Glu Ala Tyr Met Thr Met Lys Ile Arg Asn
145                 150                 155                 160


<210> SEQ ID NO 2
<211> LENGTH: 160
<212> TYPE: PRT
<213> ORGANISM: Mus musculus

<400> SEQUENCE: 2

Ser Arg Gly Gln Tyr Ser Arg Glu Asp Asn Asn Cys Thr His Phe Pro
1               5                   10                  15

Val Gly Gln Ser His Met Leu Leu Glu Leu Arg Thr Ala Phe Ser Gln
            20                  25                  30

Val Lys Thr Phe Phe Gln Thr Lys Asp Gln Leu Asp Asn Ile Leu Leu
        35                  40                  45

Thr Asp Ser Leu Met Gln Asp Phe Lys Gly Tyr Leu Gly Cys Gln Ala
    50                  55                  60

Leu Ser Glu Met Ile Gln Phe Tyr Leu Val Glu Val Met Pro Gln Ala
65                  70                  75                  80

Glu Lys His Gly Pro Glu Ile Lys Glu His Leu Asn Ser Leu Gly Glu
                85                  90                  95

Lys Leu Lys Thr Leu Arg Met Arg Leu Arg Arg Cys His Arg Phe Leu
            100                 105                 110

Pro Cys Glu Asn Lys Ser Lys Ala Val Glu Gln Val Lys Ser Asp Phe
        115                 120                 125

Asn Lys Leu Gln Asp Gln Gly Val Tyr Lys Ala Met Asn Glu Phe Asp
    130                 135                 140

Ile Phe Ile Asn Cys Ile Glu Ala Tyr Met Met Ile Lys Met Lys Ser
145                 150                 155                 160


<210> SEQ ID NO 3
<211> LENGTH: 145
<212> TYPE: PRT
<213> ORGANISM: Unknown
<220> FEATURE:
<223> OTHER INFORMATION: viral form of IL-10 (vIL-10)

<400> SEQUENCE: 3

Gln Cys Asp Asn Phe Pro Gln Met Leu Arg Asp Leu Arg Asp Ala Phe
1               5                   10                  15

Ser Arg Val Lys Thr Phe Phe Gln Thr Lys Asp Glu Val Asp Asn Leu
            20                  25                  30

Leu Leu Lys Glu Ser Leu Leu Glu Asp Phe Lys Gly Tyr Leu Gly Cys
        35                  40                  45

Gln Ala Leu Ser Glu Met Ile Gln Phe Tyr Leu Glu Glu Val Met Pro
    50                  55                  60

Gln Ala Glu Asn Gln Asp Pro Glu Ala Lys Asp His Val Asn Ser Leu
65                  70                  75                  80

Gly Glu Asn Leu Lys Thr Leu Arg Leu Arg Leu Arg Arg Cys His Arg
                85                  90                  95

Phe Leu Pro Cys Glu Asn Lys Ser Lys Ala Val Glu Gln Ile Lys Asn
            100                 105                 110

Ala Phe Asn Lys Leu Gln Glu Lys Gly Ile Tyr Lys Ala Met Ser Glu
        115                 120                 125

Phe Asp Ile Phe Ile Asn Tyr Ile Glu Ala Tyr Met Thr Ile Lys Ala
    130                 135                 140

Arg
```

```
145


<210> SEQ ID NO 4
<211> LENGTH: 9
<212> TYPE: PRT
<213> ORGANISM: Artificial Sequence
<220> FEATURE:
<223> OTHER INFORMATION: IL-10 fragment

<400> SEQUENCE: 4

Ala Tyr Met Thr Met Lys Ile Arg Asn
1               5


<210> SEQ ID NO 5
<211> LENGTH: 9
<212> TYPE: PRT
<213> ORGANISM: Artificial Sequence
<220> FEATURE:
<223> OTHER INFORMATION: IL-10 variants
<220> FEATURE:
<221> NAME/KEY: MISC_FEATURE
<222> LOCATION: (1)..(1)
<223> OTHER INFORMATION: Xaa = Ala or Gly
<220> FEATURE:
<221> NAME/KEY: MISC_FEATURE
<222> LOCATION: (2)..(2)
<223> OTHER INFORMATION: Xaa = Tyr or Phe
<220> FEATURE:
<221> NAME/KEY: MISC_FEATURE
<222> LOCATION: (3)..(3)
<223> OTHER INFORMATION: Xaa = Met, Ile, Leu or Val
<220> FEATURE:
<221> NAME/KEY: MISC_FEATURE
<222> LOCATION: (5)..(5)
<223> OTHER INFORMATION: Xaa = Met, Ile, Leu or Val
<220> FEATURE:
<221> NAME/KEY: MISC_FEATURE
<222> LOCATION: (7)..(7)
<223> OTHER INFORMATION: Xaa = Met, Ile, Leu or Val
<220> FEATURE:
<221> NAME/KEY: MISC_FEATURE
<222> LOCATION: (9)..(9)
<223> OTHER INFORMATION: Xaa = Asp, Gln or Gly

<400> SEQUENCE: 5

Xaa Xaa Xaa Thr Xaa Lys Xaa Arg Xaa
1               5
```

METHOD FOR DELIVERING GENES

CROSS-REFERENCE TO RELATED APPLICATION

This application is a 35 U.S.C. §371 filing of PCT/US2006/020864, filed May 26, 2006, from which priority is claimed under 35 U.S.C. §120, which in turn claims the benefit under 35 USC §119(e)(1) of provisional application 60/686,324, filed May 31, 2005, which applications are hereby incorporated by reference in their entireties.

STATEMENT REGARDING FEDERALLY SPONSORED RESEARCH OR DEVELOPMENT

This invention was made with government support under grant numbers DA015642, DA17656 and HL56510 awarded by the National Institutes of Health. The government has certain rights in the invention.

TECHNICAL FIELD

The present invention relates generally to gene delivery methods. In particular, the present invention pertains to methods of gene delivery using plasmids comprising adeno-associated virus (AAV) inverted terminal repeat sequences to achieve sustained expression of the gene in a target cell.

BACKGROUND

Gene therapy using genetically engineered cells and viruses has undergone impressive development over the past 40 years. Gene therapy techniques have been applied to diverse medical problems and have been used in over 350 clinical trials (Wu et al., *Meth. Strat. Anesthes.* (2001) 94:1119-1132).

Gene therapy has been attempted using various virus particles, including recombinant adeno-associated virus (rAAV) virions encoding therapeutic transgenes. Recombinant AAV vectors can be readily constructed using techniques well known in the art. See, e.g., U.S. Pat. Nos. 5,173,414 and 5,139,941; International Publication Nos. WO 92/01070 and WO 93/03769; Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875. Although such AAV virion-mediated gene delivery has been shown to give rise to long term expression of transgenes in target cells, and long term therapeutic benefit in animal models, rAAV virus particles can generate an adverse immune response in human subjects. In addition, the packaging limit for AAV virions is approximately 5000 bases, which limits the size of the transgene construct that can be delivered using such virions.

Gene therapy vectors derived from other viruses have disadvantages as well. A number of retroviral-based gene delivery systems have been described. See, e.g., U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Retroviral virion-mediated gene therapy, however, can result in integration of the transgene into the chromosome of the target cell at a random location, which could create an undesirable mutation.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993)67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476). Adenovirus virion-mediated gene therapy, however, is plagued by potentially serious immune response in humans.

As an alternative to viral vectors, plasmid DNA (pDNA) has also been used as a vector for gene delivery, as described in U.S. Pat. Nos. 6,413,942; 6,214,804; 5,580,859; 5,589,466; 5,763,270; and 5,693,622, the disclosures of which are hereby incorporated by reference in their entireties. Plasmids have an advantage viral vectors because the production of sufficient quantities of virions at sufficiently high titer is difficult and expensive. Plasmids will include the gene of interest operably linked to control elements that direct the expression of the protein product in vivo. Such control elements are well known in the art. Transgene expression is dependent on several features of the plasmid. The transcription of the transgene is controlled by the enhancer/promoter sequences, acting singly or in combination, incorporated into the sequence of the pDNA. Stability of the transcribed message is enhanced by the presence of a poly-adenylation signal at the 3' end of the transcript, known as the polyA tail. Transcription termination sequences may also be of importance, as are other regulatory domains, such as internal ribosome entry sites ("IRES"), and the like, which collectively provide for the replication, transcription and translation of a coding sequence in a recipient cell. Not all of these control sequences need always be present so long as the selected coding sequence is capable of being replicated, transcribed and translated in an appropriate host cell.

Plasmid-mediated gene therapy, however, has typically only directed transient, rather than sustained, transgene expression in target cells.

The need exists for improved methods of gene therapy that are capable of directing sustained transgene expression without the adverse consequences and expense associated with virion-mediated gene therapy methods.

SUMMARY OF THE INVENTION

The present invention is based on the surprising discovery that sustained expression of a transgene can be achieved by plasmid transfection using a plasmid encoding one or more AAV inverted terminal repeat (ITR) sequences. The AAV ITR is equally effective whether it is located upstream or downstream of the transgene within the plasmid sequence.

In one embodiment the plasmid comprises exactly two AAV ITR sequences. In other embodiment the plasmid comprises a single AAV ITR sequence.

In an exemplary embodiment, pain can be successfully treated in an acceptable pain model by delivering a gene encoding the anti-inflammatory cytokine IL-10 using such plasmids. Such treatment prevents and reverses pain, such as neuropathic pain, including mechanical allodynia, without affecting basal pain responsivity to mechanical stimuli.

Accordingly, in one embodiment, the invention is related to delivery of a transgene to a target cell using a plasmid encoding one or more ITRs and a transgene. In some embodiments this delivery results in sustained expression of the transgene in the target cell. In some embodiments the transgene is a therapeutic transgene. In additional embodiments transgene expression results in improvement in a pathological condition in a disease model. In yet additional embodiments transgene expression results in a therapeutic effect.

In some embodiments, the ITR is derived from a virus selected from the group consisting of an AAV, adenovirus, retrovirus and lentivirus. In one embodiment, the ITR is an AAV-2 ITR.

In other embodiments, the invention is directed to a method of treating pain, such as neuropathic pain, in a vertebrate subject comprising administering to the nervous system of the subject a plasmid encoding one or more AAV ITRs and encoding an agent selected from the group consisting of an anti-inflammatory cytokine, a proinflammatory cytokine antagonist, and an agent that acts to reduce or prevent proinflammatory cytokine actions, operably linked to expression control elements, under conditions that result in expression of the agent in vivo to reduce pain. In one embodiment the one or more ITRs are AAV ITRs.

In certain embodiments, the agent is one or more agents selected from the group consisting of interleukin-10 (IL-10), interleukin-1 receptor antagonist (IL-1ra), interleukin-4 (IL-4), interleukin-13 (IL-13), tumor necrosis factor soluble receptor (TNFsr), alpha-MSH, and transforming growth factor-beta 1 (TGF-β1).

In yet further embodiments, the vertebrate subject is a human and the anti-inflammatory cytokine is human IL-10.

In additional embodiments, the administering is by intraparenchymal, intrathecal or epidural delivery. In one embodiment the administering is by intrathecal delivery.

In another embodiment, the method further comprises administering, at five days or less after the first dose, such as three days or less, a second dose of the plasmid encoding one or more ITRs and encoding an agent selected from the group consisting of an anti-inflammatory cytokine, a proinflammatory cytokine antagonist, and an agent that acts to reduce or prevent inflammatory cytokine actions, operably linked to expression control elements, under conditions that result in expression of the agent in vivo to maintain reduced pain. In one embodiment the one or more ITRs are AAV ITRs.

In certain embodiments, the vertebrate subject is a human and the IL-10 is human IL-10.

In certain embodiments of the invention, the IL-10 gene is fused to a sequence encoding the Fc portion of an IgG.

In other embodiments, the invention is directed to a composition comprising a plasmid encoding a single ITR and further encoding a therapeutic agent selected from the group consisting of an anti-inflammatory cytokine, a proinflammatory cytokine antagonist, and an agent that acts to reduce or prevent proinflammatory cytokine actions, operably linked to expression control elements, under conditions that result in expression of the therapeutic agent in vivo to reduce pain. In some embodiments the ITR is an AAV ITR.

In yet other embodiments, the invention relates to methods of treatment of neuropathic pain using a composition comprising a plasmid encoding a single ITR and further encoding a therapeutic agent selected from the group consisting of an anti-inflammatory cytokine, a proinflammatory cytokine antagonist, and an agent that acts to reduce or prevent proinflammatory cytokine actions, operably linked to expression control elements, under conditions that result in expression of the therapeutic agent in vivo to reduce pain. In some embodiments the single ITR is an AAV ITR.

These and other embodiments of the subject invention will readily occur to those of skill in the art in view of the disclosure herein.

BRIEF DESCRIPTION OF THE FIGURES

FIG. 10 shows a comparison of the amino acid sequences of mature secreted forms of human IL-10 (hIL-10) (SEQ ID NO:1), mouse IL-10 (mIL-10) (SEQ ID NO:2) and a viral form of IL-10 (vIL-10) (SEQ ID NO:3). Amino acid residues differing from the human sequence are boxed.

DETAILED DESCRIPTION OF THE INVENTION

Figure 1:
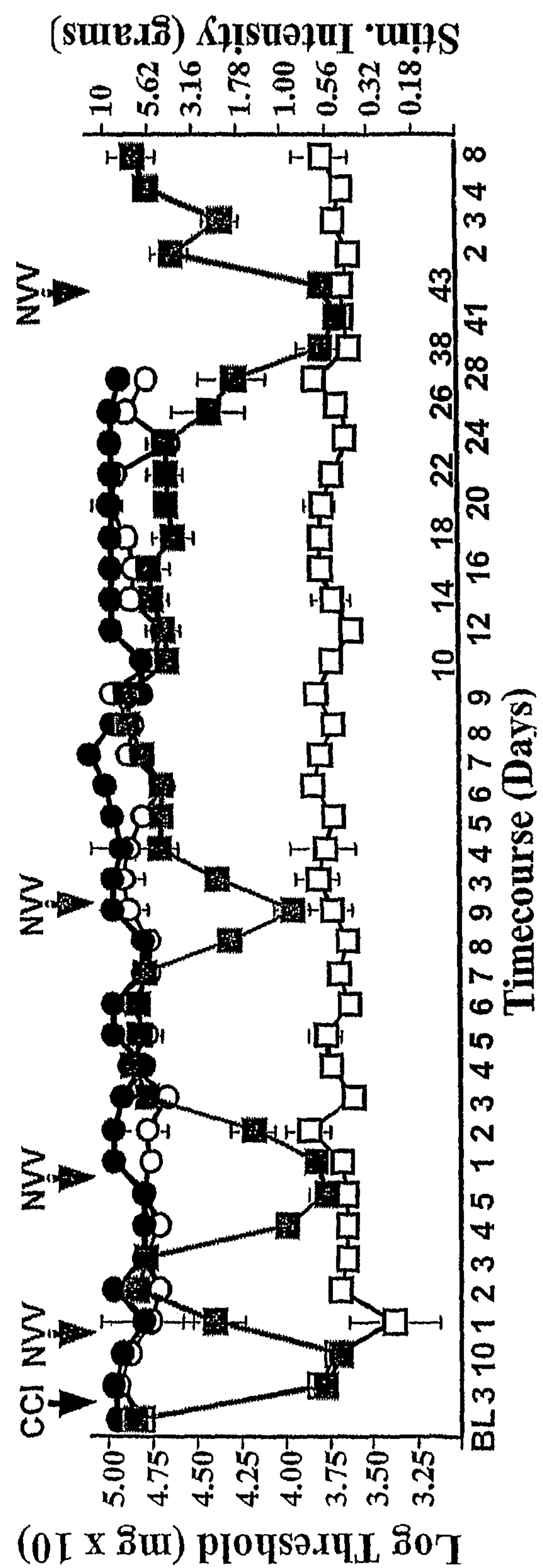
FIG. 1 shows that non-viral vector (NVV) plasmid DNA-driven IL-10 completely reverses CCI-induced mechanical allodynia and that repeated intrathecal administration of plasmid IL-10 induces progressively longer pain-relieving effects. After baseline (BL), CCI was induced and rats were given intrathecal injections of either plasmid IL-10 or plasmid GFP as a control at the time-points indicated in the figure by arrows. Filled squares indicate CCI rats administered plasmid IL-10; open squares indicate CCI rats administered the GFP control plasmid; filled circles indicate sham operated rats given plasmid IL-10; open circles indicate sham operated rats administered GFP control plasmid.

The present invention relates to use of inverted terminal repeat (ITR) containing plasmid DNAs (pDNAs) as an exceptionally effective means by which neuropathic pain conditions in rats can be reversed. pDNAs that contain two ITR regions are most effective, but single ITR-containing pDNAs are also effective, with durations of effect lasting greater than 1 month and often as long as 2 or more months. See FIG. 9. Removal of both ITRs from the pDNA renders the pDNA ineffective in treating pain. See FIGS. 8, 9. This extension of therapeutic efficacy of plasmids should be beneficial in a variety of long term or progressively degenerative conditions, whether originating within the central nervous system or of systemic origin.

In the experiments reported herein, an AAV ITR is used, but ITRs are a common feature of viral genomes across multiple viral lineages. These sequences contain some promoter activities. Their primary functions appear to be the control of both the efficient replication and packaging of the viral genome and the integration of the viral genome into the host cell genome. The surprising result presented herein is that one or more AAV ITRs are also necessary and sufficient for sustained gene expression from plasmid gene therapy vectors in, vivo.

The illustrative examples presented herein are directed to the treatment of neuropathic pain, but the invention is generally applicable to treatment of any disorder in which sustained transgene expression may be beneficial. Although the exemplary experiments disclosed herein involve intrathecal delivery of a transgene encoding IL-10 to the CNS, other delivery modes to other target tissues can be used. A summary of the general therapeutic approach of administration of IL-10 for the treatment of neuropathic pain is described in greater detail in WO 05/000215, the disclosure of which is hereby incorporated by reference in its entirety.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology,* 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein are hereby incorporated by reference in their entirety

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an anti-inflammatory cytokine" includes a mixture of two or more such cytokines, and the like.

By "pathological pain" is meant any pain resulting from a pathology, such as from functional disturbances and/or pathological changes, injuries, lesions, burns and the like. One form of pathological pain is "neuropathic pain." The term "neuropathic pain" as used herein refers to pain caused by, but not limited to, a neuropathy, an encephalopathy and/or a myelopathy (i.e., functional disturbances or pathological states of the peripheral nervous system, brain and spinal cord, respectively). Neuropathic pain can be caused by nerve damage, injury such as spinal cord injury, neuritis, inflammation, noninflammatory lesions, electrical injuries, headaches, and the like. Neuropathic pain can also be caused by complications of various diseases, including without limitation, demyelinating diseases, diabetes, amyloid diseases, porphyric diseases, Lyme disease, leprosy, acromegaly, rheumatoid arthritis, autoimmune diseases, metabolic diseases, cancer, and viral infection. Such pain can also be caused by toxic states, such as but not limited to, toxic states caused by arsenic, isoniazid, lead and nitrofurantoin. Examples of neuropathic pain include, but are not limited to, thermal or mechanical hyperalgesia, thermal or mechanical allodynia, diabetic pain, pain arising from irritable bowel or other internal organ disorders, endometriosis pain, phantom limb pain, complex regional pain syndromes, fibromyalgia, low back pain, cancer pain, pain arising from infection, inflammation or trauma to peripheral nerves or the central nervous system, multiple sclerosis pain, entrapment pain, pain from HIV infection, herpesvirus infection, and the like.

"Hyperalgesia" means an abnormally increased pain sense, such as pain that results from an excessive sensitiveness or sensitivity.

"Hypalgesia" (or "hypoalgesia") means the decreased pain sense.

"Allodynia" means pain that results from a non-noxious stimulus to the skin. Examples of allodynia include, but are not limited to, cold allodynia, tactile allodynia, and the like.

"Nociception" is defined herein as pain sense. "Nociceptor" herein refers to a structure that mediates nociception. The nociception may be the result of a physical stimulus, such as, mechanical, electrical, thermal, or a chemical stimulus. Nociceptors are present in virtually all tissues of the body.

"Analgesia" is defined herein as the relief of pain without the loss of consciousness. An "analgesic" is an agent or drug useful for relieving pain, again, without the loss of consciousness.

The term "nervous system" includes both the central nervous system and the peripheral nervous system." The term "central nervous system" or "CNS" includes all cells and tissue of the brain and spinal cord of a vertebrate. The term "peripheral nervous system" refers to all cells and tissue of the portion of the nervous system outside the brain and spinal cord. Thus, the term "nervous system" includes, but is not limited to, neuronal cells, glial cells, astrocytes, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, cells in the epineurium, perineurium, endoneurium, funiculi, fasciculi, and the like.

The term "anti-inflammatory cytokine" as used herein refers to a protein that decreases the action or production of one or more proinflammatory cytokines or proteins produced by nerves, neurons, glial cells, endothelial cells, fibroblasts, muscle, immune cells or other cell types. Such inflammatory cytokines and proteins include, without limitation, interleukin-1 beta (IL-1β), tumor necrosis factor-alpha (TNF-α), interleukin-6 (IL-6), inducible nitric oxide synthetase (iNOS) and the like. Non-limiting examples of anti-inflammatory cytokines include interleukin-10 (IL-10) including viral IL-10, interleukin-4 (IL-4), interleukin-13 (IL-13), alpha-MSH, transforming growth factor-beta 1 (TGF-β1), and the like. All of these anti-inflammatory cytokines, as well as active fragments, and active analogs thereof, which retain the ability to decrease pain as measured in any of the known pain models including those described further herein, are intended for use with the present invention.

Thus, the full-length proteins and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification.

Accordingly, active proteins substantially homologous to the parent sequence, e.g., proteins with 70 . . . 80 . . . 85 . . . 90 . . . 95 . . . 98 . . . 99% etc. identity that retain the ability to reduce pain, are contemplated for use herein.

By "proinflammatory cytokine antagonist" is meant any molecule that blocks or antagonizes the biologic action of a proinflammatory cytokine, such as by binding or interacting with a proinflammatory cytokine receptor thereby reducing or inhibiting the production of the proinflammatory cytokine. The terms "antagonist", "inhibitor", and "blocker" are used interchangeably herein. Non-limiting examples of such antagonists include interleukin-1 receptor antagonist (IL-1ra); KINERET (recombinant IL-1ra, Amgen); tumor necrosis factor soluble receptor (TNFsr); soluble TNF receptor Type I (Amgen); pegylated soluble TNF receptor Type I (PEGs TNF-R1) (Amgen); TNF decoy receptors; ETANERCEPT (ENBREL, Amgen); INFLIXIMAB (REMICADE, Johnson & Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; ONERCEPT, a recombinant TNF binding protein (r-TBP-1) (Serono); IL1-Receptor Type 2 (Amgen), AMG719 (Amgen) and IL-1 Trap (Regeneron).

All of these proinflammatory cytokine antagonists, as well as active fragments, and active analogs thereof, which retain the ability to decrease pain as measured in any of the known pain models including those described further herein, are intended for use with the present invention.

Thus, the full-length molecules and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70 . . . 80 . . . 85 . . . 90 . . . 95 . . . 98 . . . 99% etc. identity that retain the ability to reduce pain, are contemplated for use herein.

By "an agent that acts to reduce inflammatory cytokine actions" is meant an agent that induces anti-inflammatory cytokine production. Such agents include, without limitation, IL-9, Hsp27 (see, U.S. Patent Publication No. 2001/0049357).

The term "therapeutic agent" as used herein refers to a protein that has the ability to decrease pain as measured in any of the known pain models including those described further herein, regardless of whether or not such agent has any therapeutic effect in any particular vertebrate subject.

All of these agents, as well as active fragments, and active analogs thereof, which retain the ability to decrease pain as measured in any of the known pain models including those described further herein, are intended for use with the present invention.

Thus, the full-length molecules and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70 . . . 80 . . . 85 . . . 90 . . . 95 . . . 98 . . . 99% etc. identity that retain the ability to reduce pain, are contemplated for use herein.

The term "analog" refers to biologically active derivatives of the reference molecule, or fragments of such derivatives, that retain the ability to reduce pain. In general, the term "analog" refers to compounds having a native polypeptide sequence and structure with one or more amino acid additions, substitutions and/or deletions, relative to the native molecule. Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M.O. in *Atlas of Protein Sequence and Structure* M.O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *supra; DNA Cloning, supra; Nucleic Acid Hybridization, supra.*

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N-6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3 prime (3')" or "5 prime (5')" relative to another sequence, it is to be understood that it is the position of the sequences in the "sense" or "coding" strand of a DNA molecule that is being referred to as is conventional in the art.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "effective amount" or "therapeutically effective amount" of a composition or agent, as provided herein, refer to a nontoxic but sufficient amount of the composition or agent to provide the desired response, such as a reduction or reversal of pain. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treatment" or "treating" pain includes: (1) preventing pain, i.e. causing pain not to develop or to occur with less intensity in a subject that may be exposed to or predisposed to pain but does not yet experience or display pain, (2) inhibiting pain, i.e., arresting the development or reversing pain, or (3) relieving pain, i.e., decreasing the amount of pain experienced by the subject.

By "treating existing pain" is meant relieving or reversing pain in a subject that has been experiencing pain for at least 24 hours, such as for 24-96 hours or more, such as 25 . . . 30 . . . 35 . . . 40 . . . 45 . . . 48 . . . 50 . . . 55 . . . 65 . . . 72 . . . 80 . . . 90 . . . 96 . . . 100, etc. hours. The term also intends treating pain that has been occurring long-term, such as for weeks, months or even years.

The term "sustained" as used with reference to the expression of a transgene in a target cell from a plasmid comprising one or more ITRs, refers to a period of expression longer than would be achieved using the same plasmid lacking any ITR sequence. For example, in various embodiments, sustained expression refers to expression of a transgene in vivo longer than 1, 2, 3, 4, 5, 7, 10, 15, 20, 25, 30, 40, 50, 60, 70 or more days. In embodiments of the invention related to treatment of neuropathic pain, for example, sustained expression can be measured using a relevant pain model such as the CCI-rat model, and the von Frey filament test, as described in more detail in the Examples.

2. Exemplary Modes of Carrying Out the Invention

In one exemplary embodiment, the present invention makes use of anti-inflammatory cytokines, proinflammatory cytokine antagonists and agents that act to reduce or prevent inflammatory cytokine action to treat pain, such as pathological and neuropathic pain. Particularly preferred anti-inflammatory cytokines and antagonists for use with the present invention include, without limitation, interleukin-10 (IL-10), interleukin-1 receptor antagonist (IL-1ra), interleukin-4 (IL-4), interleukin-13 (IL-13), tumor necrosis factor soluble receptor (TNFsr), alpha-MSH and transforming growth factor-beta 1 (TGF-β1). The native molecules, as well as fragments and analogs thereof, which retain the ability to decrease pain as measured in any of the known pain models including those described further herein, are intended for use with the present invention. One particularly preferred IL-10 molecule for use herein includes a fusion of IL-10 to the Fc portion of an IgG, described in more detail below. Moreover, sequences derived from any of numerous species can be used with the present invention, depending on the animal to be treated.

For example, a number of sequences related to IL-10, as well as IL-10 fragments, variants and agonists, which function to reduce pain will also find use herein. For example, sequences related to IL-10 are described in, e.g., International Publication Nos. WO 00/65027; WO 98/28425; WO 95/24425 (immunomodulator Trichinella substances). International Publication No. WO 95/03411 describes shortened IL-10 sequences, variants and agonists of IL-10 having amino acid substitutions or deletions at the carboxyl and/or amino terminus of mature human sequence; U.S. Pat. No. 6,428,985 describes IL-10 variants with a substitution of Ile at position 87 of the mature human IL-10 sequence with Ala or Gly; U.S. Pat. No. 6,159,937 describes an IL-10 fragment with the sequence Ala-Tyr-Met-Thr-Met-Lys-Ile-Arg-Asn) (SEQ ID NO:4); International Publication No. WO 97/26778 describes IL-10 variants with the sequence X1-X2-X3-Thr-X4-Lys- X5-Arg-X6 (SEQ ID NO:5) where X1=Ala or Gly; X2=Tyr or Phe; X3, X4 and X5 are independently selected from Met, Ile, Leu and Val; and X6=Asp, Gln or Gly.

Nucleotide and amino acid sequences of anti-inflammatory cytokines, proinflammatory cytokine antagonists and agents that act to reduce or prevent inflammatory cytokine action, and variants thereof, from several animal species are well known. For example, IL-10 has been isolated from a number of animal and viral species. IL-10 for use herein includes IL-10 from any of these various species. Non-limiting examples of viral IL-10 include the IL-10 homologues isolated from the herpesviruses such as from Epstein-Barr virus (see, e.g., Moore et al., *Science* (1990) 248:1230-1234; Hsu et al., *Science* (1990) 250:830-832; Suzuki et al., *J. Exp. Med.* (1995) 182:477-486), Cytomegalovirus (see, e.g., Lockridge et al., *Virol.* (2000) 268:272-280; Kotenko et al., *Proc. Natl. Acad. Sci. USA* (2000) 97:1695-1700; International Publication No. WO 01/16153), and equine herpesvirus (see, e.g., Rode et al., *Virus Genes* (1993) 7:111-116), as well as the IL-10 homologue from the OrF virus (see, e.g., Imlach et al., *J. Gen. Virol.* (2002) 83:1049-1058 and Fleming et al., *Virus Genes* (2000) 21:85-95). See, also, FIG. 10 herein depicting the amino acid sequence of a mature, secreted form of viral IL-10. Representative, non-limiting examples of other IL-10 sequences for use with the present invention include the sequences described in NCBI accession numbers NM000572, U63015, AF418271, AF247603, AF247604, AF247606, AF247605, AY029171, UL16720 (all human sequences), and FIG. 10 herein depicting the amino acid sequence of a mature secreted form of human IL-10; NM012854, L02926, X60675 (rat); NM010548, AF307012, M37897, M84340 (all mouse sequences), and FIG. 10 herein depicting the amino acid sequence of a mature secreted form of mouse IL-10; U38200 (equine); U39569, AF060520 (feline sequences); U00799 (bovine); U11421, Z29362 (ovine sequences); L26031, L26029 (macaque sequences); AF294758 (monkey); U33843 (canine); AF088887, AF068058 (rabbit sequences); AF012909, AF120030 (woodchuck sequences); AF026277 (possum); AF097510 (guinea pig); U11767 (deer); L37781 (gerbil); AB107649 (llama and camel).

Non-limiting examples of IL-1ra sequences for use with the present invention include the sequences described in NCBI accession numbers NM173843, NM173842, NM173841, NM000577, AY196903, BC009745, AJ005835, X64532, M63099, X77090, X52015, M55646 (all human sequences); NM174357, AB005148 (bovine sequences); NMO31167, S64082, M57525, M644044 (mouse sequences); D21832, 568977, M57526 (rabbit sequences); SEG AB045625S, M63101 (rat sequences); AF216526, AY026462 (canine sequences); U92482, D83714 (equine sequences); AB038268 (dolphin).

Non-limiting examples of IL-4 sequences for use with the present invention include the sequences described in NCBI accession numbers NM172348, AF395008, AB015021, X16710, A00076, M13982, NM000589 (all human sequences); BC027514, NM021283, AF352783, M25892 (mouse sequences); NM173921, AH003241, M84745, M77120 (bovine sequences); AY130260 (chimp); AF097321, L26027 (monkey); AY096800, AF172168, Z11897, M96845 (ovine sequences); AF035404, AF305617 (equine sequences); AF239917, AF187322, AF054833, AF104245 (canine sequences); X16058 (rat); AF046213 (hamster); L07081 (cervine); U39634, X87408 (feline); X68330, L12991 (porcine sequences); U34273 (goat); AB020732 (dolphin); L37779 (gerbil); AF068058, AF169169 (rabbit sequences); AB107648 (llama and camel).

Non-limiting examples of IL-13 sequences for use with the present invention include the sequences described in NCBI accession numbers NM002188, U10307, AF377331, X69079 (all human sequences); NM053828, L26913 (rat sequences); AF385626, AF385625 (porcine sequences); AF244915 (canine); NM174089 (bovine); AY244790 (monkey); NM008355 (mouse); AB107658 (camel); AB107650 (llama).

Non-limiting examples of TGF-β1 sequences for use with the present invention include the sequences described in NCBI accession numbers NM000660, BD0097505, BD0097504, BD0097503, BD0097502 (all human sequences); NM021578, X52498 (rat sequences); AJ009862, NM011577, BC013738, M57902 (mouse sequences); AF461808, X12373, M23703 (porcine sequences); AF175709, X99438 (equine sequences); X76916 (ovine); X60296 (hamster); L34956 (canine).

Non-limiting examples of alpha-MSH sequences for use with the present invention include the sequences described in NCBI accession number NM000939 (human); NM17451 (bovine); NM008895 (mouse); and M11346 (xenopus).

Non-limiting examples of TNF receptor sequences for use with the present invention include the sequences described in NCBI accession numbers X55313, M60275, M63121, NM152942, NM001242, NM152877, NM152876, NM152875, NM152874, NM152873, NM152872, NM152871, NM000043, NM001065, NM001066, NM148974, NM148973, NM148972, NM148971, NM148970, NM148969, NM148968, NM148967, NM148966, NM148965, NM003790, NM032945, NM003823, NM001243, NM152854, NM001250 (all human sequences); NM013091, M651122 (rat sequences).

Non-limiting examples of IL-9 sequences for use with the present invention include the sequences described in NCBI accession numbers NM000590 (human) and NM008373 (mouse).

Plasmids encoding the desired anti-inflammatory cytokine, proinflammatory cytokine antagonist and agents that act to reduce or prevent inflammatory cytokine for use with the present invention can be made using standard techniques of molecular biology. For example, plasmids coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 223:1299; and Jay et al., *J. Biol. Chem.* (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Natl. Acad. Sci. USA* (1991) 88:4084-4088. Additionally, oligonucleotide-directed synthesis (Jones et al., *Nature*

(1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Natl. Acad. Sci. USA* (1989) 86:10029-10033) can be used to provide molecules for use in the subject methods.

Gene Delivery Techniques

Plasmids of the present invention, also referred to herein as non-viral vectors (NVV), can be administered using any of the several plasmid delivery techniques well-known in the art. For example, vectors can be introduced without delivery agents, as described in, e.g., U.S. Pat. Nos. 6,413,942, 6,214,804 and 5,580,859, all incorporated by reference herein in their entireties.

Alternatively, the plasmids encoding the gene of interest can be packaged in liposomes prior to delivery to the subject or to cells derived therefrom, such as described in U.S. Pat. Nos. 5,580,859; 5,549,127; 5,264,618; 5,703,055, all incorporated herein by reference in their entireties. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527. The DNA can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488, incorporated herein by reference in their entireties.

The plasmids may also be encapsulated, adsorbed to, or associated with, particulate carriers, well known in the art. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368.

Moreover, plasmid DNA can be guided by a nuclear localization signal or like modification.

Additionally, biolistic delivery systems employing particulate carriers such as gold and tungsten, are useful for delivering genes of interest. The particles are coated with the gene to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744, all incorporated herein by reference in their entireties.

A wide variety of other methods can be used to deliver the plasmid vectors. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al., supra, for a discussion of techniques for transforming cells of interest; and Feigner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451,002, 6,418,341, 6233,483, U.S. Patent Publication No. 2002/0146831; and International Publication No. WO/0045823, all of which are incorporated herein by reference in their entireties.

It may also be desirable to fuse the plasmid encoding the gene of interest to immunoglobulin molecules in order to provide for sustained expression. One convenient technique is to fuse the plasmid encoding the agent of interest to the Fc portion of a mouse IgG2a with a noncytolytic mutation. Moreover, in one embodiment, an IL-10 gene can be present in the form of a fusion protein, fused to the Fc portion of an IgG. Such a technique has been shown to provide for sustained expression of cytokines, such as IL-10, especially when combined with electroporation. See, e.g., Jiang et al., *J. Biochem.* (2003) 133:423-427; and Adachi et al., *Gene Ther.* (2002) 2:577-583.

Adeno-Associated Virus ITRs

ITR sequences for use in the present invention can be obtained from viruses, including AAV. AAV has been used with success to deliver genes for gene therapy. The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology,* 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. AAV ITRs can also be derived from AAV variants isolated from other species, such as mouse, goat and cow. Furthermore, AAV ITRs in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, ITR sequences are obtained from adenovirus. Adenoviral ("Ad") DNA contains identical Inverted Terminal Repeats ("ITRs") of about 100 base pairs with the exact length depending on the serotype. The viral origins of replication are located within the ITRs exactly at the genome ends. "Minimal" adenovirus vectors are described in U.S. Pat. No. 6,306,652. Such vectors retain at least a portion of the viral genome that is required for encapsidation of the genome into virus particles (the encapsidation signal), as well as at least one copy of at least a functional part or a derivative of the ITR.

In yet another embodiment, murine leukemia retroviruses long terminal repeats (LTRs) are used in place of the ITR sequences in the plasmids of the present invention. Murine leukemia retroviruses include a single strand RNA complexed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs).

Recombinant AAV Expression Vectors

Recombinant AAV (rAAV) expression vector plasmids are constructed using known techniques to at least provide as operatively linked components in the direction of transcription, control elements including a transcriptional initiation region, the anti-inflammatory polynucleotide of interest and a transcriptional termination region. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Leblcowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158: 97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

The control elements are selected to be functional in a target cell. In one embodiment, the resulting construct which contains the operatively linked components is bounded (5' and 3') with functional AAV ITR sequences. In other embodiments, one of the AAV ITRs is removed.

AAV has been engineered to deliver genes of interest by deleting the internal nonrepeating portion of the AAV genome (i.e., the rep and cap genes) and inserting a heterologous gene (in this case, the gene encoding the anti-inflammatory cytokine) between the ITRs. The heterologous gene is typically functionally linked to a heterologous promoter (constitutive, cell-specific, or inducible) capable of driving gene expression in the patient's target cells under appropriate conditions. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

Termination signals, such as polyadenylation sites, can also be included. Recombinant AAV vectors comprising a transgene of interest, for example a sequence encoding an anti-inflammatory cytokine, may be produced using a variety of art-recognized techniques in the field of molecular biology.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. In yet another alternative, a single AAV ITR is fused to either the 5' or 3' end of the selected nucleic acid construct. For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors that contain ITRs have been described in, e.g., U.S. Pat. No. 5,139,941. Several AAV vectors described therein are available from the American Type Culture Collection ("ATCC") under Accession Numbers 53222, 53223, 53224, 53225 and 53226.

Exemplary Transgenes

In addition to IL-10, the list of potential transgenes to be delivered using an ITR-containing plasmid of the present invention includes, but is not limited to: glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain alpha-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding ornithine transcarbamylase, associated with ornithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase (ADA), associated with severe combined immunodeficiency disease; DNA encoding hypoxanthine guanine phosphoribosyl transferase, associated with Gout and Lesch-Nyan syndrome; DNA encoding biotimidase, associated with biotimidase deficiency; DNA encoding beta-glucocerebrosidase, associated with Gaucher disease; DNA encoding beta-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding alpha-1 antitrypsin for treatment of alpha-1 antitrypsin deficiency (emphysema); DNA encoding erythropoietin (EPO) for treatment of anemia due to thalassemia or to renal failure; DNA encoding vascular endothelial growth factor (VEGF), DNA encoding angiopoietin-1, and DNA encoding fibroblast growth factor for the treatment of ischemic diseases; DNA encoding thrombomodulin and tissue factor pathway inhibitor (TFPI) for the treatment of occluded blood vessels as seen in, for example, atherosclerosis, thrombosis, or embolisms; DNA encoding aromatic amino acid decarboxylase (AADC), and DNA encoding tyrosine hydroxylase (TH) for the treatment of Parkinson's disease; DNA encoding the beta adrenergic receptor, DNA encoding anti-sense to, or DNA encoding a mutant form of, phospholamban, DNA encoding the sarco(endo)plasmic reticulum adenosine triphosphatase-2 (SERCA2), and DNA encoding the cardiac adenylyl cyclase for the treatment of congestive heart failure; DNA encoding a tumor suppressor gene such as p53 for the treatment of various cancers; DNA encoding a cytokine such as one of the various interleukins for the treatment of inflammatory and immune disorders and cancers; DNA encoding dystrophin or minidystrophin and DNA encoding utrophin or miniutrophin for the treatment of muscular dystrophies; and, DNA encoding insulin for the treatment of diabetes.

The invention also relates to ITR-containing plasmids comprising a gene or genes coding for blood coagulation proteins, which genes may be delivered using the methods of the present invention, to the cells of a mammal for the treatment of hemophilia or other blood clotting disorder. Thus, the invention includes: delivery of the Factor IX gene to a mammal for treatment of hemophilia B, delivery of the Factor VIII gene to a mammal for treatment of hemophilia A, delivery of the Factor VII gene for treatment of Factor VII deficiency, delivery of the Factor X gene for treatment of Factor X deficiency, delivery of the Factor XI gene for treatment of Factor XI deficiency, delivery of the Factor XIII gene for treatment of Factor XIII deficiency, and, delivery of the Protein C gene for treatment of Protein C deficiency. Thus, the invention includes ITR-containing plasmids comprising genes encoding any one of Factor IX, Factor VIII, Factor X, Factor VII, Factor XI, Factor XIII or Protein C.

Exemplary transgenes also include, but are not limited to: sFLT-1; interleukin-1 receptor antagonist (IL-1ra); interleukin-4 (IL-4); interleukin-13 (IL-13); tumor necrosis factor soluble receptor (TNFsr); alpha-MSH; transforming growth factor-beta 1 (TGF-.beta.1); interleukin-1 receptor; interleukin-1 soluble receptor; tumor necrosis factor soluble receptor; interferon-alpha; the osteoclast inhibitor osteoprotegerin; glial cell line-derived neurotrophic factor polypeptide (GDNF); guanosine triphosphate cyclohydrolase; 6-pyruvoyl-tetrahydropterin synthase; dihydropteridine reductase; arginine-vasopressin (AVP); Cox-1; E2F-1; E2F-2A; E2F-2B; PGIS; Cox-1(2A); Cox-2(2B); ENOS; TIMP-1; TIMP-2; and the genes implicated in well known genetic defects such as cystic fibrosis (CFTR), Hurler's Disease, and emphysema.

Compositions and Delivery

A. Compositions

Once produced, the plasmid DNA vectors encoding the transgene of interest will be formulated into compositions suitable for delivery. In one embodiment directed to the treatment of neuropathic pain, compositions will comprise sufficient genetic material to produce a therapeutically effective amount of the anti-inflammatory cytokine of interest, i.e., an amount sufficient to reduce or ameliorate pain. The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

One particularly useful formulation comprises the plasmid DNA vector of interest in combination with one or more dihydric or polyhydric alcohols, and, optionally, a detergent, such as a sorbitan ester. See, for example, International Publication No. WO 00/32233.

As is apparent to those skilled in the art in view of the teachings of this specification, an effective amount can be empirically determined. Representative doses are detailed below. Administration can be effected in one dose, continuously or intermittently throughout the course of treatment. Methods of determining the most effective means and dosages of administration are well known to those of skill in the art and will vary with the vector, the composition of the therapy, the target cells, and the subject being treated. Single and multiple administrations can be carried out with the dose level and pattern being selected by the treating physician.

As shown in the examples below, one particularly effective way to produce long-term alleviation of pain involves administering two or more doses of ITR-containing plasmid encoding IL-10 at close intervals, e.g., at less than 10 days apart, preferably less than 5 days apart, more preferably less than 4 days apart, such as at 3 . . . 2 . . . 1 . . . etc. and any amount of time within the stated ranges.

It should be understood that more than one transgene can be expressed by the delivered plasmid. For example, the recombinant vectors can encode more than one anti-inflammatory cytokine. Alternatively, separate plasmids, each expressing one or more different transgenes, can also be delivered to the nervous system as described herein. Thus, multiple anti-inflammatory cytokines can be delivered concurrently or sequentially. Furthermore, it is also intended that the vectors delivered by the methods of the present invention be combined with other suitable compositions and therapies. For instance, other pain alleviators and analgesics, such as anti-prostaglandins, including, without limitation, cyclooxygenase-2 (COX-2) inhibitors, 5-lipoxygenase (5-LOX) inhibitors, and the like, can be coadministered with the compositions of the invention. Other compounds for delivery include agents used in the treatment of neuropathic pain such as, but not limited to, tricyclic antidepressants (e.g., amitriptyline, imipramine, desipramine), anti-convulsants (e.g., gabapentin, carbamazepine, phenyloin) and local anesthetics (e.g., mexiletine, lidocaine); and agents used in the treatment of inflammatory pain including, but not limited to, NSAIDs (e.g., ibuprofen, naprosyn sodium, aspirin, diclofenac sodium, indomethacin, toletin), steroids (e.g., methylprednisone, prednisone), analgesics (e.g., acetaminophen), and opiates (e.g., tramadol, demerol, darvon, vicodin, fentanyl).

B. Delivery

The recombinant plasmid DNA vectors of the present invention may be introduced into a target tissue by any method know in the art.

In an embodiment directed to treatment of neuropathic pain, plasmids are preferably targeted to the nervous system, including any cell or tissue of the CNS or peripheral nervous system, or cells or tissues in close proximity thereto. Thus, delivery can be, for example, into any neural tissue including, without limitation, peripheral nerves, the retina, dorsal root ganglia, neuromuscular junction, as well as the CNS, e.g., to target spinal cord glial cells, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue.

The recombinant plasmid DNA vectors are introduced either in vivo or in vitro (also termed ex vivo) to treat preexisting neuronal damage, neuropathies and other causes of neuropathic pain as defined above. If transduced in vitro, the desired recipient cell will be removed from the subject, treated with rAAV plasmids and reintroduced into the subject. Alternatively, syngeneic or xenogeneic cells can be used where those cells will not generate an inappropriate immune response in the subject. Additionally, neural progenitor cells can be treated in vitro and then delivered to the CNS.

Generally, from 1 μl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

Recombinant plasmids, or cells treated with plasmid in vitro, may be delivered directly to neural tissue such as peripheral nerves, the retina, dorsal root ganglia, neuromuscular junction, as well as the CNS, e.g., to target spinal cord glial cells, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, and the like, by injection into, e.g., the ventricular region, as well as to the striatum (e.g., the caudate nucleus or putamen of the striatum), spinal cord and neuromuscular junction, into the interstitial space, with a needle, catheter or related device, using techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000), epidural delivery, etc.

A particularly preferred method for targeting the nervous system, such as spinal cord glia, is by intrathecal delivery, rather than into the cord tissue itself. An advantage of intrathecal gene therapy is that the intrathecal route mimics lumbar puncture administration (i.e., spinal tap) already in routine use in humans.

Another method for delivery is by administration into the epidural space. The epidural space occupies the vertebral canal between the periosteum lining the canal and the dura. The epidural space is readily approached through the lumbar area. Generally, a needle, catheter or the like is inserted in the midline and passes through the skin, fascia, supraspinous and interspinous ligaments, and the ligamentum flavum prior to reaching the extradural space. However, administration can also be through the thoracic area. Methods for delivering agents epidurally are well known in the art. See, e.g., *Textbook of Surgery*, (D. C. Sabiston, ed.) W.B. Saunders Company.

Yet another mode of administration to the CNS uses a convection-enhanced delivery (CED) system. In this way, recombinant plasmid DNA vectors can be delivered to many cells over large areas of the CNS. Any convection-enhanced delivery device may be appropriate for delivery of recombinant vectors. In a preferred embodiment, the device is an osmotic pump or an infusion pump. Both osmotic and infusion pumps are commercially available from a variety of suppliers, for example Alzet Corporation, Hamilton Corporation, Alza, Inc. (Palo Alto, Calif.). Typically, a recombinant plasmid DNA vector is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. Moreover, because the methods described herein can be practiced such that relatively large areas of the subject take up the recombinant plasmid DNA vectors, fewer infusion cannula are needed. Since surgical complications are related to the number of penetrations, this mode of delivery serves to reduce the side-effects seen with conventional delivery techniques. For a detailed description regarding CED delivery, see U.S. Pat. No. 6,309,634, incorporated herein by reference in its entirety.

Moreover, the gene encoding the active agent may be fused to sequences encoding antibodies or peptides to improve stability and extend half-life, using techniques well known in the art. For example, the gene encoding the active agent may be fused to sequences encoding immunoglobulin molecules in order to provide for sustained release. One convenient technique is to fuse the gene encoding the agent of interest to a sequence encoding the Fc portion of an IgG such as a human or mouse IgG2a with a noncytolytic mutation. See, e.g., Jiang et al., *J. Biochem.* (2003) 133:423-427; Adachi et al., *Gene Ther.* (2002) 9:577-583; and U.S. Pat. No. 6,410,008, incorporated herein by reference in its entirety. A non-lytic recombinant human IL-10/Fc chimera is commercially available from Sigma Chemical Co. (St. Louis, Mo.).

One particularly effective way to produce long-term alleviation of pain involves administering two or more doses of plasmid DNA encoding IL-10 and one or more AAV ITRs at close intervals, e.g., at less than 10 days apart, preferably less than 5 days apart, more preferably less than 4 days apart, such as at 3 . . . 2 . . . 1 . . . etc. and any amount of time within the stated ranges.

Pain Models

The ability of an anti-inflammatory cytokine to treat pain can be evaluated by any of the accepted pain models known in the art. Examples of such models are as follows. Not all of the models disclosed below are used in the experiments reported herein.

Tail Flick Model: The tail-flick test (D'Amour et al., *J. Pharmacol Exp. and Ther.* (1941) 72:74-79) is a model of acute pain. A gently-restrained rat is placed on a test stage such that a focused light source beams on the dorsal or ventral surface of the rat's tail. A photosensor is present on the test stage located opposite the light source. To begin the test, the rat's tail blocks the light, thus preventing the light reaching the photosensor. Latency measurement begins with the activation of the light source. When a rat moves or flicks its tail, the photosensor detects the light source and stops the measurement. The test measures the period of time (duration) that the rat's tail remains immobile (latent). Rats are tested prior to administration thereto of a compound of interest and then at various times after such administration.

Rat Tail Immersion Model: The rat tail immersion assay is also a model of acute pain. A rat is loosely held in hand while covered with a small folded thin cotton towel with its tail exposed. The tip of the tail is dipped into a water bath (e.g. 52° C.) to a depth of two inches. The rat responds by either wiggling of the tail or withdrawal of the tail from the water; either response is scored as the behavioral end-point. Rats are tested for a tail response latency (TRL) score prior to administration thereto of a compound of interest and then retested for TRL at various times after such administration.

Carrageenan-induced Paw Hyperalgesia Model: The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al., *Arch. Int. Pharmacodyn.* (1957) 111:409-419.

The effects of selected agents on carrageenan-induced paw edema can also be examined. This test (see, Vinegar et al., *J. Phamacol. Exp. Ther.* (1969) 166:96-103) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Formalin Behavioral Response Model: The formalin test is a model of acute, persistent pain. Response to formalin treatment is biphasic (Dubuisson et al., *Pain* (1977) 4:161-174). The Phase I response is indicative of a pure nociceptive response to the irritant. Phase 2, typically beginning 20 to 60 minutes following injection of formalin, is thought to reflect increased sensitization of the spinal cord.

Von Frey Filament Test: The effect of compounds on mechanical allodynia can be determined by the von Frey filament test in rats with a tight ligation of the L-5 spinal nerve: a model of painful peripheral neuropathy. The surgical procedure is performed as described by Kim et al., *Pain* (1992) 50:355-363. A calibrated series of von Frey filaments are used to assess mechanical allodynia (Chaplan et al., *J. Neurosci. Methods* (1994) 53:55-63). Filaments of increasing stiffness are applied perpendicular to the midplantar surface in the sciatic nerve distribution of the left hindpaw. The filaments are slowly depressed until bending occurs and are then held for 4-6 seconds. The filament application order and number of trials are determined by the up-down method of Dixon (Chaplan et al., supra). Flinching and licking of the paw and paw withdrawal on the ligated side are considered positive responses.

Chronic Constriction Injury: Heat and cold allodynia responses can be evaluated as described below in rats having a chronic constriction injury (CCI). A unilateral mononeuropathy is produced in rats using the chronic constriction injury model described in Bennett et al., *Pain* (1988) 33:87-107. CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1-2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

2. EXPERIMENTAL

Below are examples of specific embodiments for carrying out the present invention. The examples are offered for illustrative purposes only, and are not intended to limit the scope of the present invention in any way.

Materials and Methods

Subjects

Pathogen-free adult male Sprague-Dawley rats (300-450 g; Harlan Labs, Madison, Wis.) were used in all experiments. Rats were housed in temperature- and light-controlled rooms with standard rodent chow and water available ad libitum. Behavioral testing was performed during the light cycle.

Plasmids

In the experiments described in Examples 1-4, plasmid DNA encoding IL-10 (pTR2-CB-rIL-10) or GFP (pTR2-CB-GFP-TK-NEO (UF11)) was subcloned and purified similar to procedures described previously (Sambrook, J, Fritsch, E. R., Maniatis, T. *Molecular cloning*, $2^{nd}$ ed., Cold Spring Harbor Press, pp 1.38-1.39, 1989). After isolation procedures, plasmids (pDNA) were dialyzed for 1 hr against DPBS (1×) and twice each for 2 hr against DPBS-3% sucrose. Dialysed pDNA preparations were stored as 300 μl aliquots at −80° C. The concentration of the pDNA-IL10 and pDNA-UF11 preparations were determined by 260 nm adsorption and were 4.2 μg/μl and 5.6 μg/μl respectively. Animals were given 100 μg pDNA for each injection day. There were a total of four injections during the 77 day experiment.

Behavioral Measures von Frey Test. The von Frey test (Chaplan et al., *J. Neurosci Meth*. (1994) 53:55-63) was performed within the sciatic and saphenous innervation area of the hindpaws as previously described (Milligan et al., *Brain Res*. (2000) 861:105-116; Chacur et al., *Pain* (2001) 94:231-244; Gazda et al., *J. Peripheral Nerv. Sys*. (2001) 6:111-129; Milligan et al., *J. Neurosci*. (2001) 21:2808-2819. Briefly, a logarithmic series of 10 calibrated Semmes-Weinstein monofilaments (von Frey hairs; Stoelting, Wood Dale, Ill.) was applied randomly to the left and right hind paws to determine the stimulus intensity threshold stiffness required to elicit a paw withdrawal response. Log stiffness of the hairs is determined by log 10(milligrams×10). The 10 stimuli had the following log-stiffness values (values in milligrams are given in parenthesis): 3.61 (407 mg), 3.84 (692 mg), 4.08 (1202 mg), 4.17 (1479 mg), 4.31 (2041 mg), 4.56 (3630 mg), 4.74 (5495 mg), 4.93 (8511 mg), 5.07 (11,749 mg), and 5.18 (15,136 mg). The range of monofilaments used in these experiments (0.407-15.136 gm) produces a logarithmically graded slope when interpolating a 50% response threshold of stimulus intensity [expressed as log 10(milligrams×10)] (Chaplan et al., *J. Neurosci Meth*. (1994) 53:55-63). Assessments were made prior to (baseline) and at specific times after peri-sciatic and intrathecal drug administration, as detailed below for each experiment. Behavioral testing was performed blind with respect to drug administration. The behavioral responses were used to calculate the 50% paw withdrawal threshold (absolute threshold), by fitting a Gaussian integral psychometric function using a maximum-likelihood fitting method (Harvey, *Behav. Res. Meth. Instrum. Comput*. (1986) 18:623-632; Treutwein and Strasburger, *Percept. Psycholphys*. (1999) 61:87-106), as described in detail previously (Milligan et al., *Brain Res*. (2000) 861:105-116). This fitting method allows parametric statistical analyses (Milligan et al., *Brain Res*. (2000) 861:105-116).

Hargreaves Test. Thresholds for behavioral response to heat stimuli applied to each hind paw were assessed using the Hargreaves test (Hargreaves et al., *Pain* (1998) 32:77-88), as previously described (Milligan et al., *Brain Res*. (2000) 861:105-116). Briefly, baseline (BL) paw withdrawal values were calculated from an average of 3-6 consecutive withdrawal latencies of both the left and right hind paws measured during a 1 hr period. Voltage to the heat source was adjusted to yield BL latencies ranging 8-12 sec and a cut off time of 20 sec was imposed to avoid tissue damage. This procedure was followed by intrathecal injections and a timecourse of post-drug behavioral assessments, as described below. Behavioral testing was performed blind with respect to drug administration. The order of paw testing varied randomly.

Surgery and Microinjections

Chronic constriction injury (CCI). CCI was created at mid-thigh level of the left hindleg as previously described (Bennett and Xie, *Pain* (1988) 33:87-107). Four sterile, absorbable surgical chromic gut sutures (cuticular 4-0, chromic gut, 27", cutting FS-2; Ethicon, Somerville, N.J.) were loosely tied around the gently isolated sciatic nerve under isoflurane anesthesia (Phoenix Pharm., St. Joseph, Mo.). The sciatic nerves of sham-operated rats were identically exposed but not ligated. Suture placements were verified at sacrifice by visual inspection. Data were only analyzed from confirmed sites.

Intrathecal microinjection of AAV plasmid into lumbosacral spinal cord. An acute catheter application method under brief isoflurane anesthesia (2% vol in oxygen) was employed. Here, a 25 cm PE-10 catheter, attached by a 30-gauge, 0.5-inch sterile needle to a sterile, 50 μl glass Hamilton syringe, was marked with black permanent ink at 7.7-7.8 cm from the open end and placed in a sterile, dry container until the time of injection. Rats were lightly anesthetized, the lower dorsal pelvic area was shaved and lightly swabbed with 70% alcohol. An 18-gauge sterile needle with the plastic hub removed was inserted between lumbar vertebrae L5 and L6. The open end of the PE-10 catheter was inserted into the 18-gauge needle and threaded to the 7.7 cm mark allowing for intrathecal PE-10 catheter-tip placement at the level of the lumbosacral enlargement. Plasmids were injected with a 1 μl pre- and post 0.9% sterile, isotonic saline solution flush for 1 min. The PE-10 catheter was immediately withdrawn and the 18-gauge needle was removed from the L5-L6 inter-vertebral space. This acute injection method took 2-3 min to complete, and rats showed full recovery from anesthesia within 10 min. No abnormal motor behavior was observed in 100% of injections.

Data Analysis

All statistical comparisons were computed using Statview 5.0.1 for the Macintosh. Data from the von Frey test were analyzed as the interpolated 50% threshold (absolute threshold) in log base 10 of stimulus intensity (monofilament stiffness in milligrams×10). Baseline measures for both the von Frey and Hargreaves tests, and dose response effects, were analyzed by one-way ANOVA. Timecourse measures for each behavioral test were analyzed by repeated measures ANOVAs followed by Fisher's protected least significant difference posthoc comparisons, where appropriate.

Example 1

Reversal of Chronic Constriction Injury (CCI) Neuropathic Pain with Intrathecally Injected Plasmid DNA Encoding for IL-10

In order to determine whether the effect of IL-10 could be elicited by delivery using a non-viral vector (NVV), the following experiment was conducted. 100 μg of plasmid ("naked") DNA (PDNA) encoding either rat IL-10 or GFP (as a control) was injected intrathecally 10 days, 15 days (five days after the first injection), 24 days (nine days after the second injection) and 67 days (43 days after the third injection) later. As shown in FIG. 1, the first injection completely but only briefly reversed pathological pain in the rats. The second injection, given after return to baseline, again completely reversed pain, but for a longer time. The third injection, given after return to baseline, again completely reversed pain but for an even longer time period. Remarkably, the fourth injection, given after the allodynia was fully reestablished for six days (Days 38-43 in FIG. 1), again completely reversed pain. The control plasmid had no effect in the CCI or sham operated rats. Given that equal doses of the control GFP plasmid had no effect on CCI, the results appear specific for IL-10.

Figure 2:
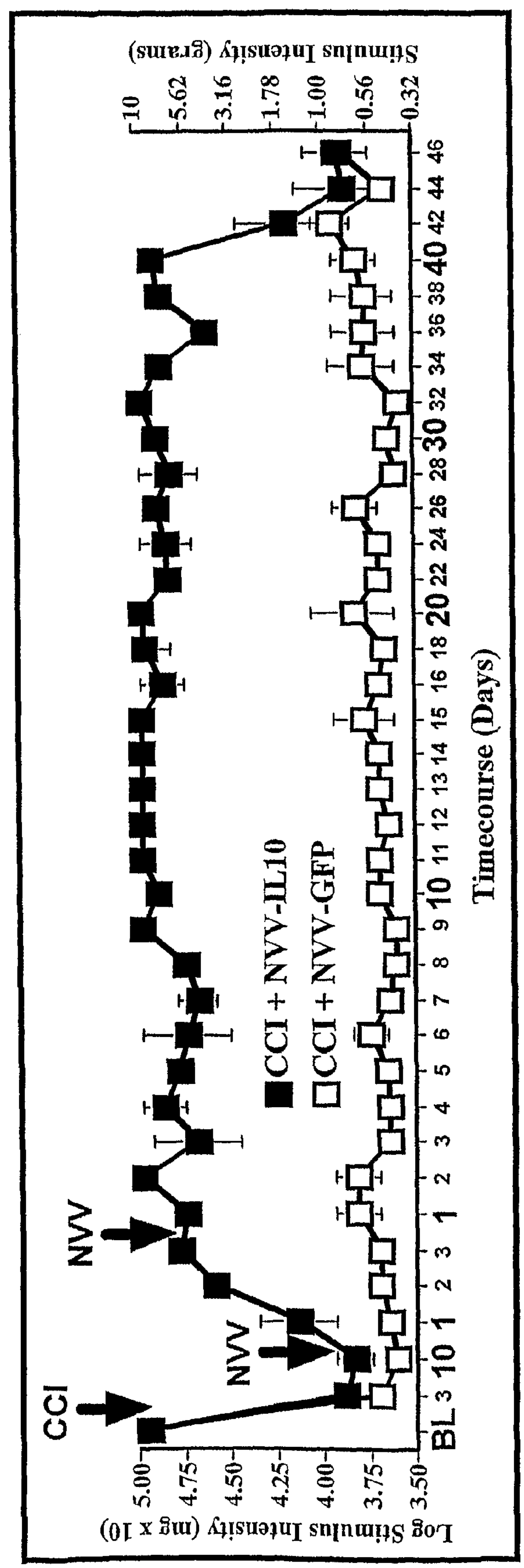
FIG. 2 shows that two doses of plasmid DNA-driven IL-10 delivery three days apart induces prolonged attenuation of CCI induced mechanical allodynia. Plasmid IL-10 was injected intrathecally at Day 10 after CCI and three days later. Filled squares indicate the results using plasmid IL-10 while open squares show the results of control plasmid.

These data raised the question of what might happen if the inter-injection interval for successive plasmid administrations were further shortened. Therefore, 100 μg of pDNA encoding rat IL-10 was injected intrathecally 10 days after CCI induced mechanical allodynia (Day 10). This induced full reversal of allodynia by Day 12 (FIG. 2). A second intrathecal injection of 100 μg of the plasmid was given on Day 13, while CCI pain-enhancement remained fully reversed, as opposed to the experiment shown in FIG. 1 and described above where the second plasmid injection was given after allodynia was allowed to reoccur. As shown in FIG. 2, when the second plasmid injection was delivered while CCI pain-enhancement remained fully reversed, the effectiveness of the second injection was remarkably enhanced.

Figure 3:
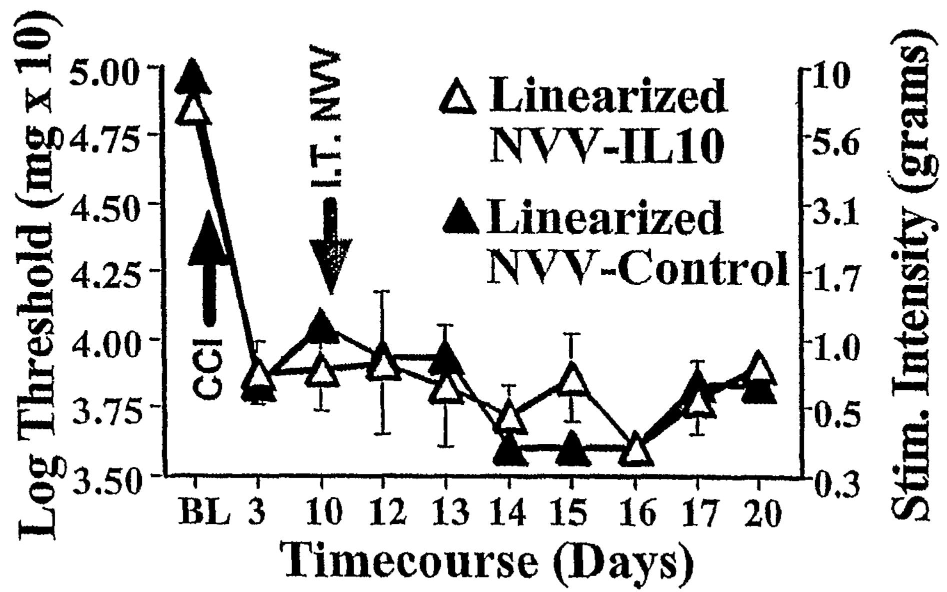
FIG. 3 shows that when the IL-10 plasmid from the experiment described in FIG. 2 is linearized, it is no longer effective in attenuating CCI induced mechanical allodynia.

As a further control, the IL-10 and GFP control plasmids were enzymatically cut to linearize them. Linearized plasmids are known to be far more susceptible to enzymatic degradation and show little to no activity. As expected, an equal dose of linearized plasmid had no effect on CCI (FIG. 3).

Example 2

FcIL-10 Enhances the Effectiveness of Gene Therapy

Figure 4:
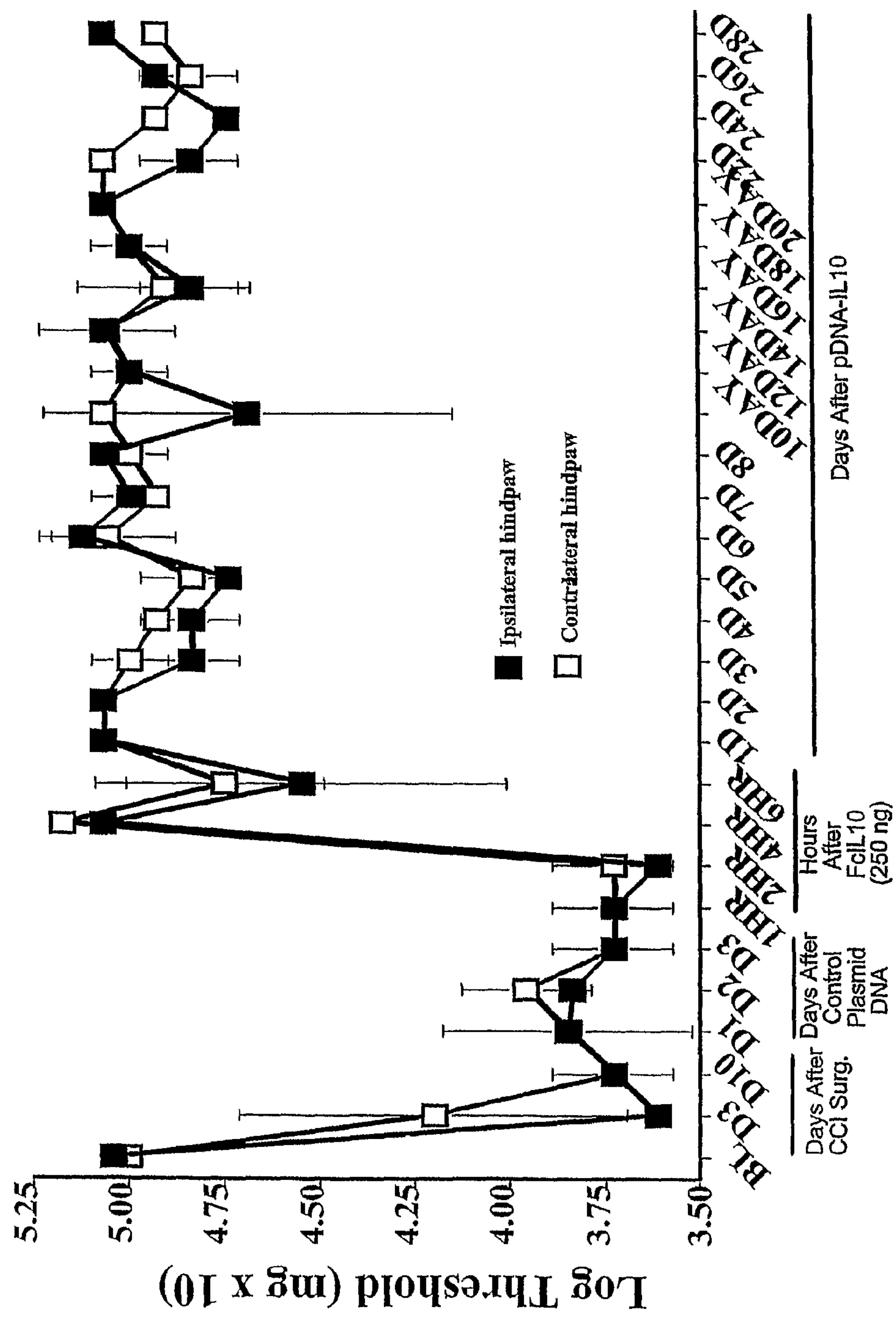
FIG. 4 shows that FcIL-10 is effective in enhancing reversal of mechanical allodynia when co-administered with a gene therapy vector, here shown with a plasmid encoding for IL-10. After baseline (BL) testing, rats received CCI surgery. They were re-tested 3 and 10 days later to verify that CCI induced profound neuropathic pain on both measures. After the Day 10 test, rats were injected i.t. with a control plasmid that did not encode IL-10; rather, it encoded for an inert intracellular protein (GFP). The presence of inert plasmid DNA did not affect behaviors tested the subsequent days. After the Day 13 test, rats were injected with either: (a) only plasmid encoding for IL-10 or (b) an equal amount of plasmid encoding for IL-10 plus a stabilized variant of IL-10 (FcIL-10) to test whether the presence of FcIL-10 would enhance vector efficacy. Indeed it does. Mechanical allodynia was reversed by plasmid-IL-10 alone for approximately 4 days. In contrast, the co-treatment with FcIL-10 remarkably enhanced both the onset and duration of plasmid-IL-10 efficacy on mechanical allodynia.

The present experiment illustrates the therapeutic efficacy of IL-10 delivered closely in time with a gene therapy vector. After baseline (BL) testing, rats received CCI surgery. They were re-tested 3 and 10 days later to verify that CCI induced profound neuropathic pain (FIG. 4). After the Day 10 test, rats were injected i.t. with a control plasmid that did not encode IL-10; rather, it encoded for an inert intracellular protein (GFP). It can be seen that the presence of inert plasmid DNA did not affect behaviors tested the subsequent days. After the Day 13 test, rats were injected with either: (a) only plasmid encoding for IL-10 or (b) an equal amount of plasmid encoding for IL-10 plus a stabilized variant of IL-10 (FcIL-10) to test whether the presence of FcIL-10 would enhance vector efficacy. Indeed it did. Mechanical allodynia was reversed by plasmid-IL-10 alone for approximately 4 days (see, the effect of the first injection of plasmid-IL-10 shown in FIG. 1). In contrast, the co-treatment with FcIL-10 remarkably enhanced both the onset and duration of plasmid-IL 10 efficacy on mechanical allodynia.

Example 3

Figure 5A:
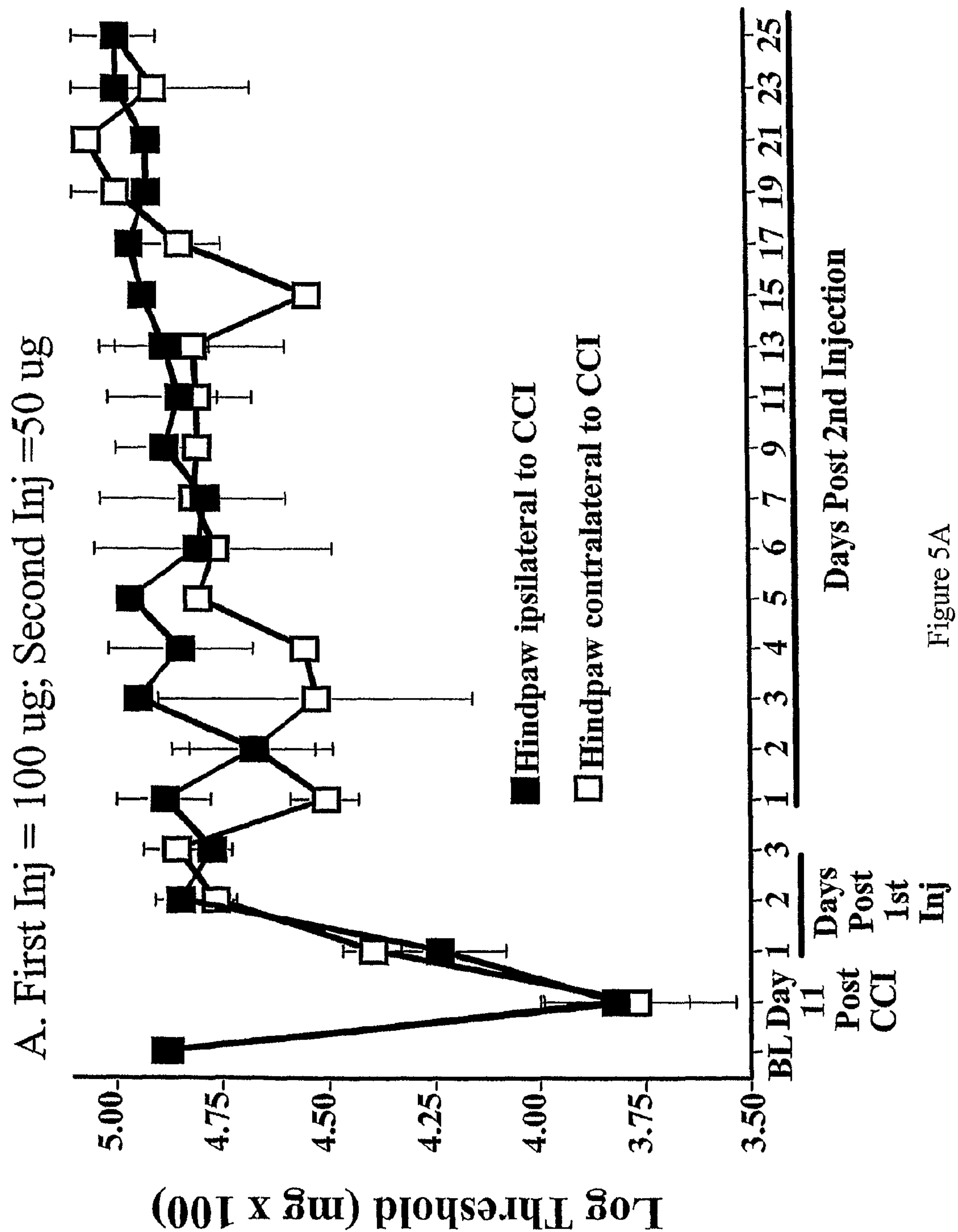
FIGS. 5A, 5B and 5C show that lower doses and dose combinations of plasmid IL-10 gene therapy effectively reverse CCI-induced mechanical allodynia. After baseline (BL) testing, rats received CCI surgery. They were re-tested 3 and 10 days later to verify that CCI induced profound neuropathic pain. Rats were then injected with either: (a) 100 μg plasmid encoding IL-10 (Day 10) followed by 50 μg plasmid encoding IL-10 (Day 13) (FIG. 5A); (b) 100 μg plasmid encoding IL-10 (Day 10) followed by 25 μg plasmid encoding IL-10 (Day 13) (FIG. 5B); or (c) 50 μg plasmid encoding IL-10 (Day 10) followed by 50 μg plasmid encoding IL-10 (Day 13) (FIG. 5C). Each led to reversal of mechanical allodynia over time.
Figure 5B:
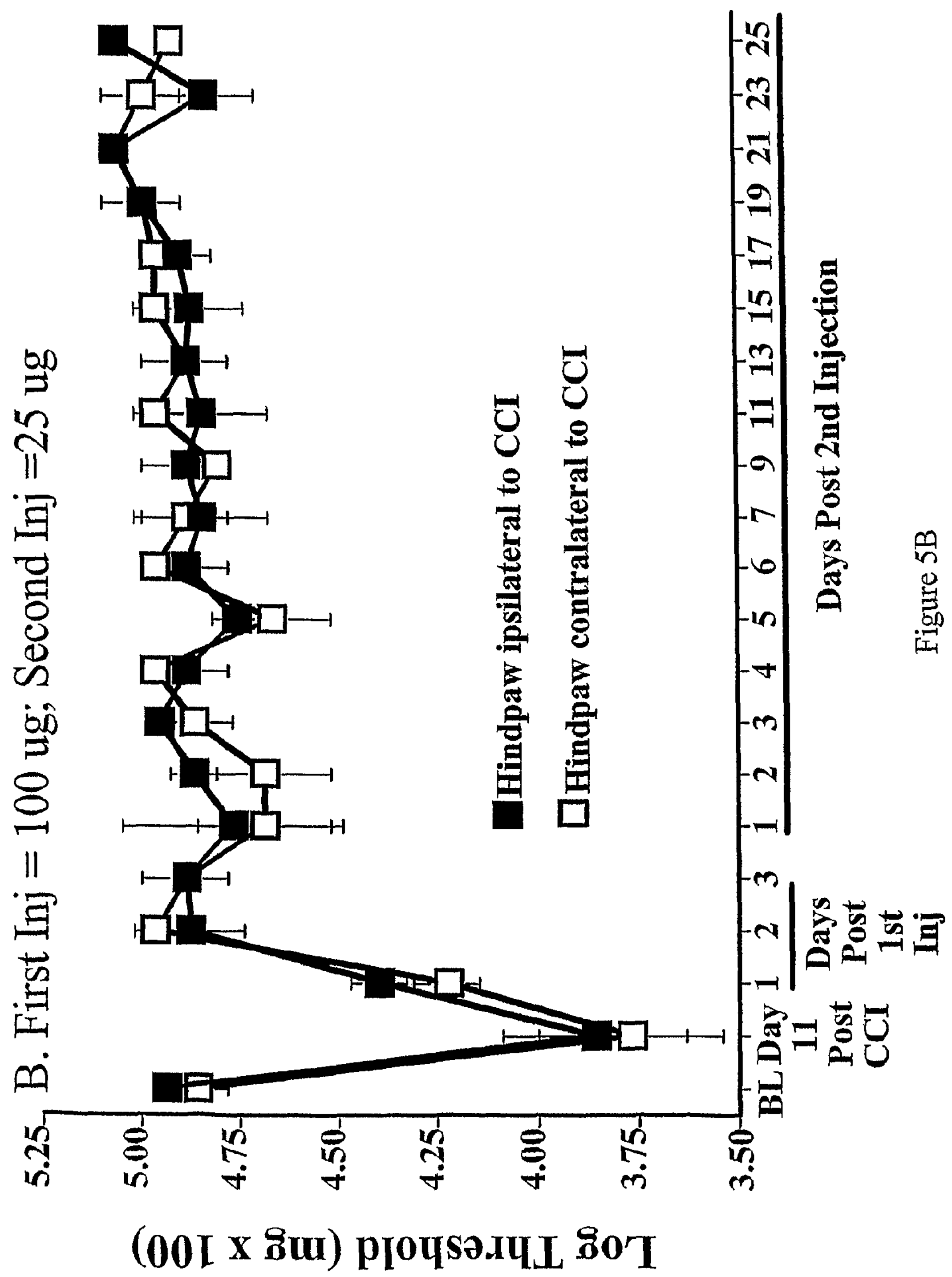
Figure 5C:
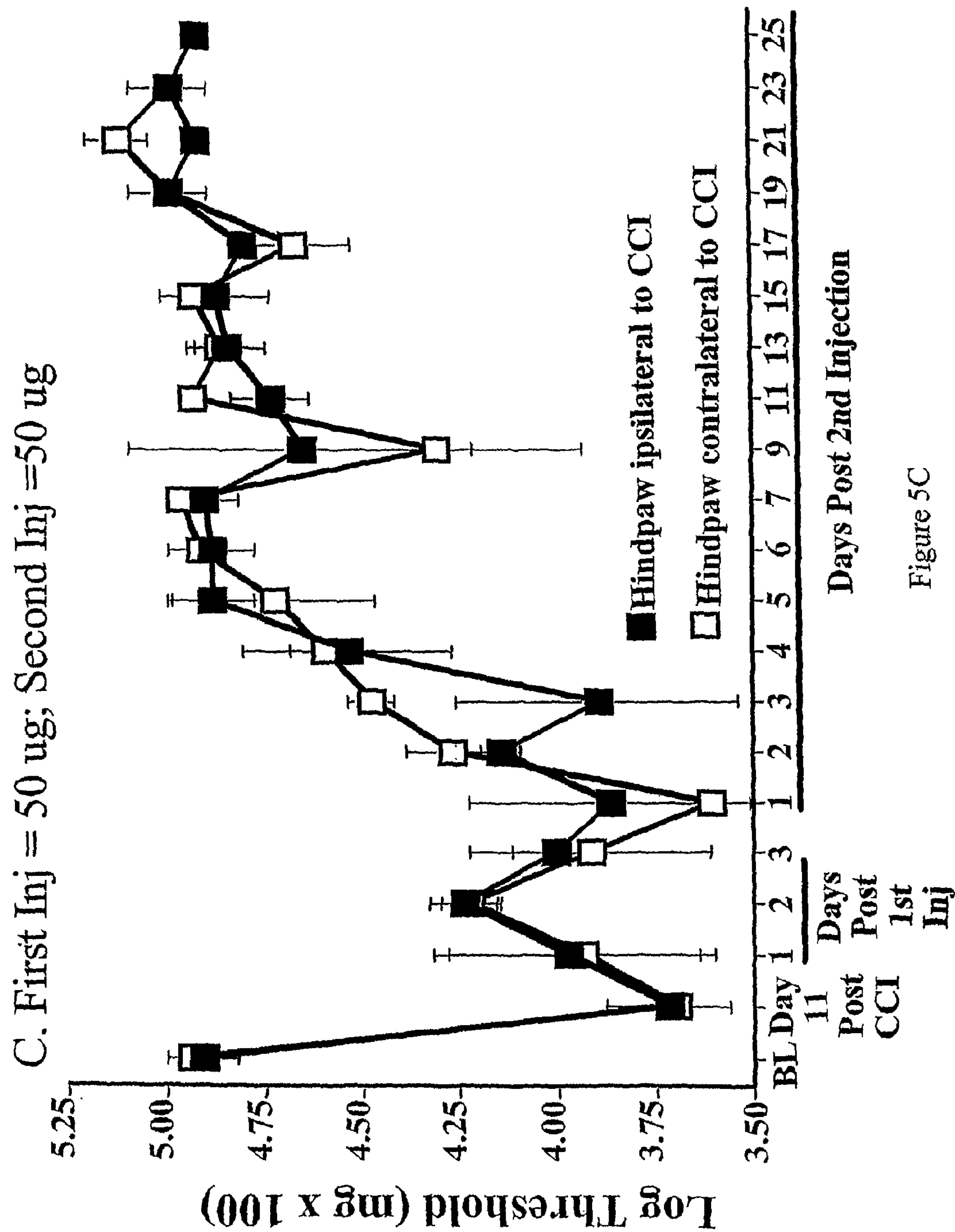

Effectiveness of Lower Doses and Dose Combinations of Plasmid IL10 Gene Therapy After baseline (BL) testing, rats received CCI surgery. They were re-tested 3 and 10 days later to verify that CCI induced profound neuropathic pain on the von Frey test (mechanical allodynia). Rats were then injected with either: (a) 100 μg plasmid encoding IL-10 (Day 10) followed by 50 μg plasmid encoding IL-10 (Day 13) (FIG. 5A); (b) 100 μg plasmid encoding IL-10 (Day 10) followed by 25 μg plasmid encoding IL-10 (Day 13) (FIG. 5B); or (c) 50 μg plasmid encoding IL-10 (Day 10) followed by 50 μg plasmid encoding IL-10 (Day 13) (FIG. 5C). As shown in the figures, each led to reversal of mechanical allodynia over time.

Example 4

The Effect of AAV ITRs on the Reversal of CCI Neuropathic Pain Using Intrathecally Injected Plasmid DNA Encoding IL-10

In order to determine the effect of AAV ITRs on the efficacy of plasmid delivery of IL-10, experiments are performed analogously with those described in Example 1. Briefly, pathogen-free adult male Sprague-Dawley rats (300-400 g) (Harlan Labs) are used in the experiments. CCI is performed by tying four loose ligatures of chromic cow gut around the sciatic nerve of the rat. Sham surgery is performed on other rats, and is similar to the CCI surgery except that no ligatures are placed around the sciatic nerve. Intrathecal injection of plasmids (pDNA) is accomplished using acute lumbar punctures. An injection catheter is temporarily inserted under brief isoflurane anesthesia (1-2% in oxygen). A PE-10 catheter is advanced through an 18-gauge needle to end at the level of the lumbosacral enlargement. The PE-10 catheter is immediately withdrawn after pDNA injection.

One consequence of neuropathic pain is that stimuli that are not normally painful become painful. A dramatic increase in sensitivity to light touch can be quantitated by recording rear paw withdrawal responses from calibrated von Frey fibers of varying stiffness. A rat that is not experiencing neuropathic pain responds to a >5 gram stimulus, whereas a rat that is experiencing neuropathic pain responds to a <1.5 gram stimulus.

Figure 6:
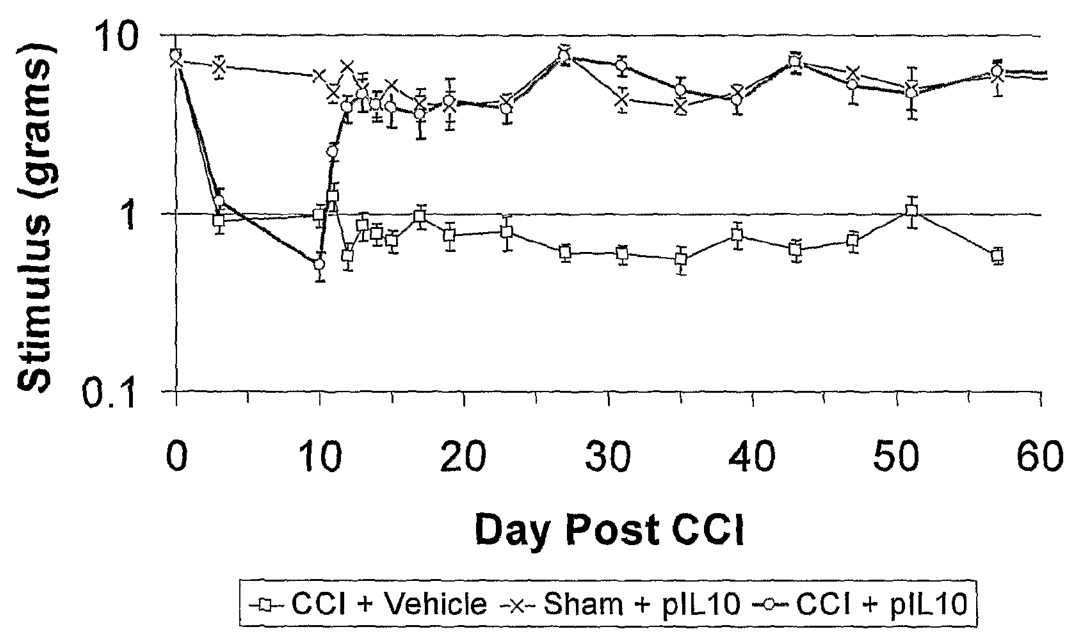
FIG. 6 shows the pain response for CCI and sham rats as a function of treatment with pIL-10, as described further at Example 4.
Figure 7:
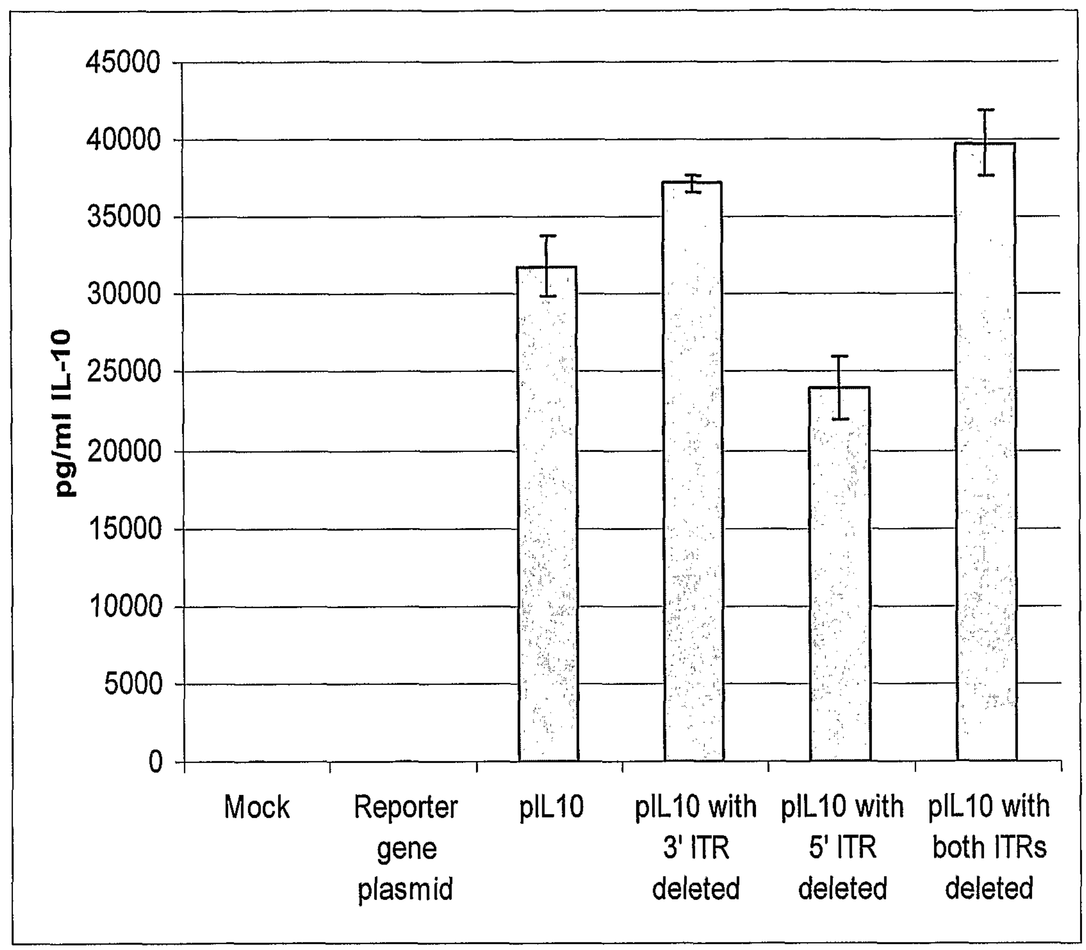
FIG. 7 shows IL-10 expression in vitro for cells transformed with no plasmid, a plasmid encoding a non-IL-10 reporter gene, and plasmids encoding IL-10 with 0, 1 or 2 AAV ITRs, as described further at Example 4.
Figure 8:
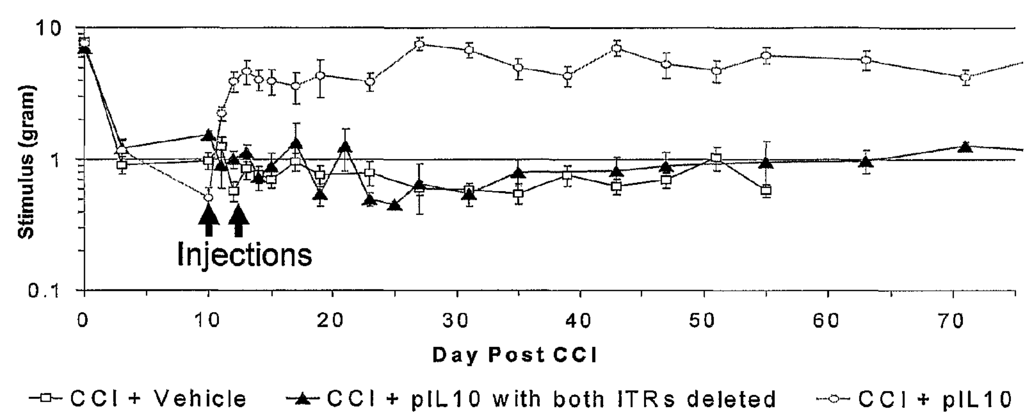
FIG. 8 shows the pain response for CCI rats as a function of treatment with pIL-10 or pIL-10 with both ITRs deleted, as described further at Example 4.
Figure 9:
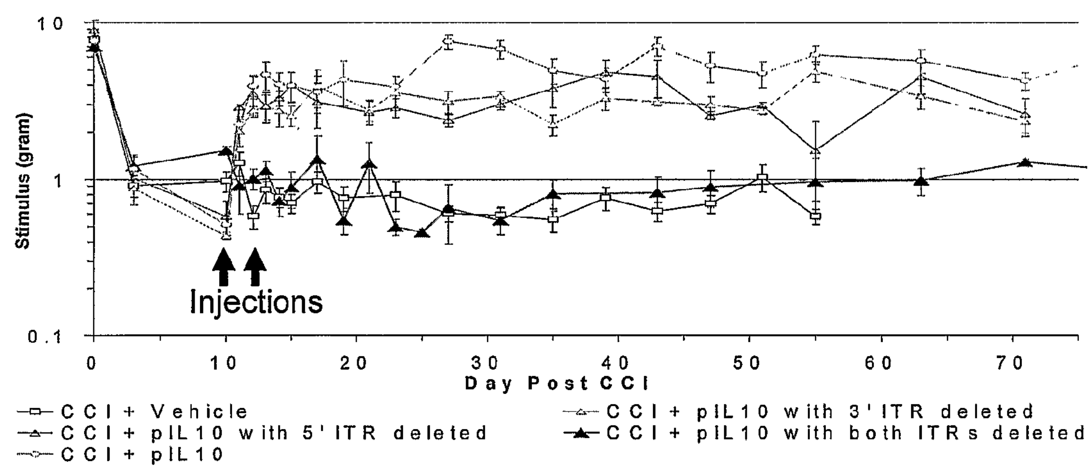
FIG. 9 shows the pain response for CCI rats as a function of treatment with pIL-10; pIL-10 with both ITRs deleted; pIL-10 with the 3' ITR; and pIL-10 with the 5' ITR deleted, as described further at Example 4.

The results of several experiments are presented at FIGS. 6-9. In FIGS. 6, 8 and 9, plasmid DNA is delivered by intrathecal injections at 10 and 13 days after chronic constriction injury of the rats, with 100 μg administered at day 10 and 25 μg at day 13.

The data presented in FIG. 6 demonstrate that intrathecal injections (i.e. injections into the cerebrospinal fluid surrounding the spinal cord) of plasmid DNA encoding IL-10 (pIL-10) and two AAV-2 ITRs (one upstream and one downstream of the IL-10 transgene) results in sustained pain reversal in chronic constriction injury (CCI) rats. In pIL-10, AAV-2 ITRs are located 5' of the CMV enhancer and Chicken β-actin promoter (5' ITR) and 3' of the SV 40 poly A tail sequence (3' ITR). Control experiments shows that pIL-10 does not change the normal pain response in non-CCI rats, and that allodynia persists throughout the course of the experiment when pIL-10 is not administered.

The data presented in FIG. 7 demonstrate that a pIL-10 is capable of directing gene expression in HEK 293 cells in vitro regardless of the presence or absence of AAV-2 ITRs. Taken in combination with the data of FIGS. 6, 8 and 9, these data demonstrate that in vitro expression of transgenes from plasmids that contain 0, 1 (either upstream or downstream) or 2 AAV-2 ITRs does not correlate with in vivo efficacy.

The data presented in FIG. 8 show that intrathecal injections of pIL-10 but lacking ITRs do not result in pain reversal in CCI rats, whereas intrathecal injections of pIL-10 result in pain reversal for over 70 days.

The data presented in FIG. 9 show that plasmid DNA encoding two AAV-2 ITRs and plasmids encoding a single ITR (either upstream or downstream of the IL-10 transgene) are effective at reversing pain for at least 70 days, whereas similar plasmids lacking ITRs do not reverse pain.

Taken together, the results presented in FIGS. 6-9 show that although plasmids lacking AAV ITRs are able to direct IL-10 expression in HEK 293 cells in vitro, at least one AAV ITR is required to achieve sustained reversal of allodynia in a CCI-rat in vivo, and that reversal of allodynia by plasmids with a single AAV ITR is effective whether the ITR is 5' or 3' of the IL-10 gene.

These surprising results show that a single AAV ITR, in either the 5' or 3' location, is necessary and sufficient to produce IL-10 expression vectors capable of producing pain reversal. In attempting to explain this surprising result, and without intending to be limited by theory, we note that published reports suggest that AAV ITRs may possess transcription promoter and enhancer activity. Flotte et al. (1992) *Am J Respir Cell Mol Biol* 7:349-56; Flotte et al. (1993) *J Biol Chem.* 268: 3781-90.

Although preferred embodiments of the subject invention have been described in some detail, it is understood that some variations can be made without departing from the spirit and the scope of the invention as defined herein. All patents and publications referred to herein are hereby incorporated by reference in their entireties.

We claim:

1. A method of treating neuropathic pain in a vertebrate subject comprising intrathecally administering to the nervous system of said subject a plasmid DNA encoding at least one adeno-associated virus (AAV) inverted terminal repeat (ITR) and further wherein the DNA encodes IL-10, operably linked to expression control elements, under conditions that result in expression of said IL-10 in vivo to reduce pain, wherein the plasmid DNA is encapsulated by a non-liposomal particulate carrier, and further wherein a single intrathecal administration of said encapsulated plasmid DNA to the vertebrate subject is capable of providing expression of IL-10 in vivo for at least 10 days.

2. The method of claim 1 wherein the plasmid DNA molecule comprises a single AAV ITR.

3. The method of claim 1, wherein the particulate carrier is a poly(lactide-co-glycolide) carrier.

4. The method of claim 1, wherein the particulate carrier is a polymethyl methacrylate carrier, or a poly(lactide) carrier.

5. The method of claim 1, wherein a single intrathecal administration of said encapsulated plasmid DNA to the vertebrate subject is capable of providing expression of IL-10 in vivo for at least 30 days.

6. A method of treating neuropathic pain in a vertebrate subject comprising intrathecally administering to the nervous system of said subject plasmid DNA encoding (1) two adeno-associated virus (AAV) inverted terminal repeats (ITRs) and (2) IL-10, operably linked to expression control elements, under conditions that result in expression of said IL-10 in vivo to reduce pain, wherein the plasmid DNA is encapsulated by a non-liposomal particulate carrier, and further wherein a single intrathecal administration of said encapsulated plasmid DNA to the vertebrate subject is capable of providing expression of IL-10 in vivo for at least 10 days.

7. The method of claim 6, wherein the particulate carrier is a poly(lactide-co-glycolide) carrier.

8. The method of claim 6, wherein the particulate carrier is a polymethyl methacrylate polymer, or a poly(lactide) carrier.

9. The method of claim 6, wherein a single intrathecal administration of said encapsulated plasmid DNA to the vertebrate subject is capable of providing expression of IL-10 in vivo for at least 30 days.

* * * * *